US012611441B2

(12) United States Patent
Bosse-Doenecke et al.

(10) Patent No.: US 12,611,441 B2
(45) Date of Patent: Apr. 28, 2026

(54) PSMA SPECIFIC BINDING PROTEINS FOR CANCER DIAGNOSIS AND TREATMENT

(71) Applicant: Navigo Proteins GmbH, Halle/Saale (DE)

(72) Inventors: Eva Bosse-Doenecke, Halle/Saale (DE); Manja Gloser-Bräunig, Halle/Saale (DE); Florian Settele, Halle/Saale (DE); Erik Fiedler, Halle/Saale (DE); Ulrich Haupts, Halle/Saale (DE)

(73) Assignee: Navigo Proteins GmbH, Halle/Saale (DE)

( * ) Notice: Subject to any disclaimer, the term of this patent is extended or adjusted under 35 U.S.C. 154(b) by 825 days.

(21) Appl. No.: 17/602,729

(22) PCT Filed: Apr. 8, 2020

(86) PCT No.: PCT/EP2020/060043
§ 371 (c)(1),
(2) Date: Oct. 8, 2021

(87) PCT Pub. No.: WO2020/208083
PCT Pub. Date: Oct. 15, 2020

(65) Prior Publication Data
US 2022/0168386 A1     Jun. 2, 2022

(30) Foreign Application Priority Data
Apr. 10, 2019     (EP) ..................................... 19168525

(51) Int. Cl.
*A61K 38/17*     (2006.01)
*C07K 14/47*     (2006.01)
*G01N 33/68*     (2006.01)

(52) U.S. Cl.
CPC .......... *A61K 38/17* (2013.01); *G01N 33/6893* (2013.01)

(58) Field of Classification Search
CPC ..... A61K 38/17; C07K 14/47; G01N 33/6893
See application file for complete search history.

(56) References Cited

U.S. PATENT DOCUMENTS 7,056,679 B2 *   6/2006  Pillutla .............. G01N 33/6845
                                                    435/7.1
2024/0309056 A1 *   9/2024  Fiedler ................... C07K 14/31

OTHER PUBLICATIONS

Definition of radiation therapy from https://www.cancer.gov/publications/dictionaries/cancer-terms/def/radiation-therapy, p. 1. Accessed Jun. 4, 2025. (Year: 2025).*
International Search Report for PCT/EP2020/060043 dated Jun. 16, 2020.
Written Opinion of the International Searching Authority for PCT/EP2020/060043 dated Jun. 16, 2020.

* cited by examiner

*Primary Examiner* — Julie Ha
(74) *Attorney, Agent, or Firm* — Jenkins, Taylor & Hunt, P.A.

(57)     ABSTRACT

Binding proteins that are specific for prostate specific membrane antigen (PSMA), multimers thereof, and conjugates thereof are described. Also described are PSMA binding proteins that include a diagnostically or therapeutically active component and/or a pharmacokinetics-modulating moiety, as well as methods for using the described PSMA binding proteins in medicine, for example, in diagnosis and therapy of cancer associated with PSMA expression.

15 Claims, 4 Drawing Sheets
Specification includes a Sequence Listing.

FIGURE 1. Structural and functional characteristics of PSMA binding proteins based on ubiquitin; motif WWNPN

| SEQ ID NO: | Affilin | 6 | 8 | 9 | 10 | 12 | 42 | 44 | 46 | 62 | 63 | 64 | 65 | 66 | 68 | 70 | 72 | further subst. | KD_PSMA Biacore in M | Thermal transition DSF in °C | cell binding |
|---|---|---|---|---|---|---|---|---|---|---|---|---|---|---|---|---|---|---|---|---|---|
| 40 | 187191 | Y | R | A | L | Q | M | F | K | W | W | N | P | N | S | N | D | (48.K>R) | 3.37E-11 | 72.62 | yes |
| 41 | 187210 | Y | R | A | L | Q | M | F | K | W | W | N | P | N | S | N | D | (33.K>R) | 2.77E-11 | 70.31 | yes |
| 42 | 187131 | Y | R | A | L | Q | M | F | K | W | W | N | P | N | S | N | G | | 5.20E-09 | 67.45 | yes |
| 43 | 187170 | Y | R | A | L | Q | M | F | K | W | W | N | P | N | S | N | N | | 7.87E-10 | 70.26 | yes |
| 44 | 187096 | Y | R | E | L | Q | M | F | K | W | W | N | P | N | S | N | D | | 3.81E-08 | 72.7 | yes |
| 50 | 187295 | Y | R | V | L | Q | M | F | K | W | W | N | P | N | S | N | D | (73.L>R) | 8.64E-14 | 63.42 | yes |
| 47 | 187134 | Y | R | V | L | Q | M | F | K | W | W | N | P | N | S | N | D | (16.E>A) | 2.43E-11 | 49.51 | yes |
| 48 | 187186 | Y | R | V | L | Q | M | F | K | W | W | N | P | N | S | N | D | (29.K>R) | 6.73E-09 | 58.68 | yes |
| 49 | 187283 | Y | R | V | L | Q | M | F | K | W | W | N | P | N | S | N | D | (71.L>R) | 3.40E-09 | 58.17 | yes |
| 36 | 187092 | Y | A | E | L | Q | M | F | K | W | W | N | P | N | S | N | D | | 1.47E-08 | 70 | yes |
| 37 | 187064 | Y | K | Q | L | Q | M | F | K | W | W | N | P | N | S | N | D | | 1.73E-09 | 70 | yes |
| 39 | 187165 | Y | R | A | L | Q | M | F | K | W | W | N | P | N | S | D | D | (23.I>V) | 4.09E-09 | 69.81 | yes |
| 38 | 187154 | Y | R | A | L | Q | M | F | K | W | W | N | P | N | S | D | D | (18.E>G).(31.Q>R) | 1.26E-09 | 68.88 | yes |
| 35 | 187093 | W | R | E | F | Q | M | F | K | W | W | N | P | N | S | N | D | | 1.46E-08 | 74 | yes |
| 51 | 187178 | Y | R | V | L | Q | T | F | R | W | W | N | P | N | S | N | D | (36.I>T) | 4.25E-13 | 53.42 | yes |

FIGURE 2. Structural and functional characteristics of PSMA binding proteins based on ubiquitin; motif KHNTW

| Affilin | 9a | 9b | 9c | 9d | 9e | 9f | 42 | 44 | 62 | 63 | 64 | 65 | 66 | 68 | 70 | 72 | further | KD_PSMA | Thermal transition | cell binding |
|---|---|---|---|---|---|---|---|---|---|---|---|---|---|---|---|---|---|---|---|---|
| 164667 | F | E | H | P | S | F | H | Y | K | H | N | T | W | E | M | F |  | 7.29E-09 | n.d. | yes |
| 161717 | F | E | H | H | S | F | H | Y | K | H | N | T | W | E | M | F |  | 4.00E-08 | 83.5 | yes |
| 161776 | F | E | H | K | S | F | H | Y | K | H | N | T | W | E | M | F |  | 4.11E-08 | 83 | yes |
| 162055 | F | E | H | N | S | F | H | Y | K | H | N | T | W | E | M | F | (46.A>V) | 3.98E-08 | 77.6 | yes |
| 162034 | P | Q | P | P | E | F | H | Y | K | H | N | T | W | E | M | F |  | 8.77E-08 | 83.5 | yes |
| 161843 | P | Q | P | P | E | W | H | Y | K | H | N | T | W | E | M | F |  | 5.17E-08 | 82.1 | yes |
| 161374 | P | Q | P | P | E | Y | H | Y | K | H | N | T | W | E | M | F |  | 4.35E-08 | 69.7 | yes |
| 162102 | P | I | P | P | D | W | H | Y | K | H | N | T | W | E | M | F |  | 6.36E-08 | 83.8 | yes |
| 161912 | P | P | F | A | F | W | H | Y | K | H | N | T | W | E | M | F |  | 7.78E-08 | 81.5 | yes |

FIGURE 3. Structural and functional characteristics of PSMA binding proteins based on ubiquitin; motif GXAHR and/or WTTTF

| SEQ ID NO: | Affilin | 1st moiety based on SEQ1 | | | | | | | 2nd moiety based on SEQ1 | | | | | | | further substitution | KD_PSMA | Thermal transition | cell binding |
|---|---|---|---|---|---|---|---|---|---|---|---|---|---|---|---|---|---|---|---|
| | | 6 | 8 | 62 | 63 | 64 | 65 | 66 | 6 | 8 | 62 | 63 | 64 | 65 | 66 | | | | |
| 3 | 162462 | R | P | G | F | A | H | R | M | Q | W | T | T | T | F | | 1.35E-08 | 78.56 | yes |
| 7 | 164052 | R | G | G | F | A | H | R | M | Q | W | T | T | T | F | | 1.67E-08 | 71.05 | yes |
| 9 | 164058 | R | I | G | F | A | H | R | M | Q | W | T | T | T | F | | 2.43E-08 | 72.61 | yes |
| 15 | 164668 | R | M | G | F | A | H | R | M | Q | W | T | T | T | F | | 4.32E-09 | 67.4 | yes |
| 8 | 161438 | R | H | S | F | A | H | R | M | R | W | T | T | T | F | | 2.33E-08 | 66 | yes |
| 19 | 161644 | R | P | S | Y | A | H | R | M | Q | W | T | T | T | F | (51.E>A) | 3.01E-08 | 70.5 | yes |
| 24 | 163970 | W | P | G | F | A | H | L | M | Q | W | T | T | T | F | | 1.10E-08 | 72.63 | yes |
| 17 | 157424 | R | P | Q | P | A | H | Q | M | Q | W | T | T | T | F | (74.R>C) | 4.06E-07 | 75.29 | yes |
| 18 | 157423 | R | P | Q | P | A | H | Q | M | R | W | T | T | T | F | | 1.67E-07 | 67.01 | yes |
| 23 | 162633 | R | W | W | W | A | D | R | M | Q | W | T | T | T | F | | 1.35E-08 | 69.4 | yes |
| 10 | 185036 | R | L | G | F | A | H | R | L | Q | W | T | P | S | I | | 2.41E-09 | 65.3 | yes |
| 12 | 191822 | R | L | G | F | A | H | R | L | Q | W | T | P | S | I | (11.K>Q).(51.E>A) | 4.38E-09 | 55.08 | yes |
| 4 | 191871 | R | Q | G | W | A | H | R | H | N | W | T | E | T | I | | 4.61E-09 | 62.81 | yes |
| 21 | 185113 | R | W | G | F | A | H | R | M | H | G | D | G | D | V | | 3.26E-07 | 82.58 | n.d. |
| 11 | 192444 | R | L | G | F | A | H | R | L | Q | W | T | P | S | I | (33.K>T).2nd: (48.K>T) | 5.35E-09 | 61.74 | yes |
| 16 | 185071 | R | M | W | G | G | H | R | L | Q | W | T | P | S | I | | 2.19E-07 | 68.71 | yes |

FIGURE 4. Functional characterization of PSMA binding proteins on PSMA-overexpressing cells (flow cytometry)
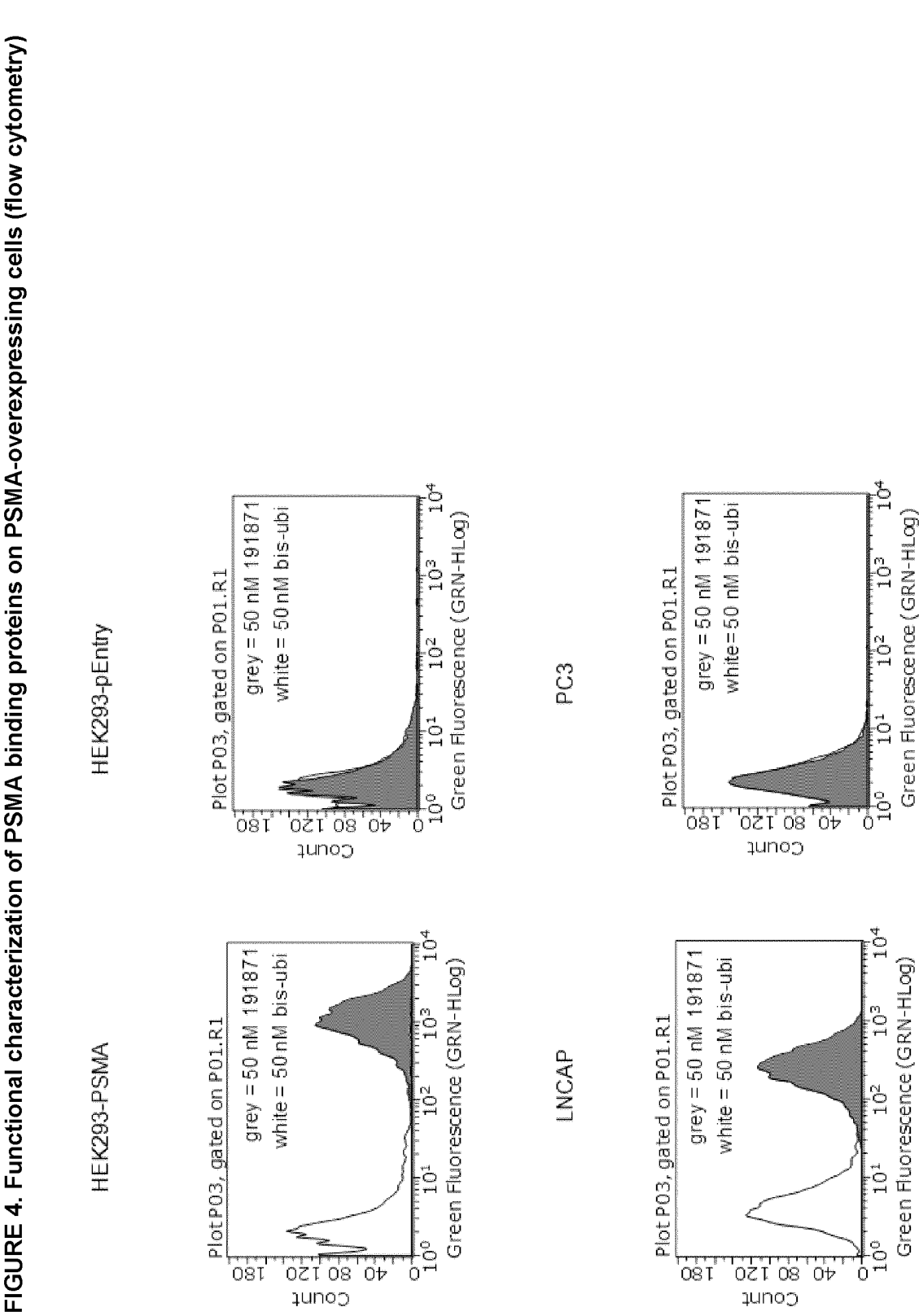

SEQUENCE LISTING

```
<160> NUMBER OF SEQ ID NOS: 86

<210> SEQ ID NO 1
<211> LENGTH: 76
<212> TYPE: PRT
<213> ORGANISM: Artificial Sequence
<220> FEATURE:
<223> OTHER INFORMATION: ubiquitin wildtype

<400> SEQUENCE: 1

Met Gln Ile Phe Val Lys Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Lys Glu
```

```
                50                    55                    60

Ser Thr Leu His Leu Val Leu Arg Leu Arg Ala Ala
65                    70                    75

<210> SEQ ID NO 2
<211> LENGTH: 152
<212> TYPE: PRT
<213> ORGANISM: Artificial Sequence
<220> FEATURE:
<223> OTHER INFORMATION: bis-ubiquitin

<400> SEQUENCE: 2

Met Gln Ile Phe Val Lys Thr Leu Thr Gly Lys Thr Ile Thr Leu Glu
1                   5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gln Lys Glu
        50                  55                  60

Ser Thr Leu His Leu Val Leu Arg Leu Arg Ala Ala Met Gln Ile Phe
65                  70                  75                  80

Val Lys Thr Leu Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Gln Lys Glu Ser Thr Leu His
    130                 135                 140

Leu Val Leu Arg Leu Arg Ala Ala
145                 150

<210> SEQ ID NO 3
<211> LENGTH: 152
<212> TYPE: PRT
<213> ORGANISM: Artificial Sequence
<220> FEATURE:
<223> OTHER INFORMATION: Affilin 162462 (CID167521)

<400> SEQUENCE: 3

Met Gln Ile Phe Val Arg Thr Pro Thr Gly Lys Thr Ile Thr Leu Glu
1                   5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gly Phe Ala
        50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125
```

```
Gly Arg Thr Leu Ser Asp Tyr Asn Ile Trp Thr Thr Thr Phe Leu His
    130                 135                 140

Leu Val Leu Arg Leu Arg Ala Ala
145                 150

<210> SEQ ID NO 4
<211> LENGTH: 152
<212> TYPE: PRT
<213> ORGANISM: Artificial Sequence
<220> FEATURE:
<223> OTHER INFORMATION: Affilin 191871

<400> SEQUENCE: 4

Met Gln Ile Phe Val Arg Thr Gln Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp Ala
    50                  55                  60

His Arg Leu His Leu Val Leu Arg Leu Arg Ala Ala Met Gln Ile Phe
65                  70                  75                  80

Val His Thr Asn Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Trp Thr Glu Thr Ile Leu His
    130                 135                 140

Leu Val Leu Arg Leu Arg Ala Ala
145                 150

<210> SEQ ID NO 5
<211> LENGTH: 155
<212> TYPE: PRT
<213> ORGANISM: Artificial Sequence
<220> FEATURE:
<223> OTHER INFORMATION: Affilin 191871 with c-terminal coupling site

<400> SEQUENCE: 5

Met Gln Ile Phe Val Arg Thr Gln Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp Ala
    50                  55                  60

His Arg Leu His Leu Val Leu Arg Leu Arg Ala Ala Met Gln Ile Phe
65                  70                  75                  80

Val His Thr Asn Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125
```

-continued

```
Gly Arg Thr Leu Ser Asp Tyr Asn Ile Trp Thr Glu Thr Ile Leu His
    130                 135                 140

Leu Val Leu Arg Leu Arg Ala Ala Ser Ala Cys
145                 150                 155

<210> SEQ ID NO 6
<211> LENGTH: 152
<212> TYPE: PRT
<213> ORGANISM: Artificial Sequence
<220> FEATURE:
<223> OTHER INFORMATION: Affilin 161421

<400> SEQUENCE: 6

Met Gln Ile Phe Val Arg Thr Asp Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gly Trp Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150

<210> SEQ ID NO 7
<211> LENGTH: 152
<212> TYPE: PRT
<213> ORGANISM: Artificial Sequence
<220> FEATURE:
<223> OTHER INFORMATION: Affilin 164052

<400> SEQUENCE: 7

Met Gln Ile Phe Val Arg Thr Gly Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
                100                 105                 110

Pro Pro Asp Gln Gln Arg Leu Ile Trp Ala Gly Lys Gln Leu Glu Asp
```

```
            115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150

<210> SEQ ID NO 8
<211> LENGTH: 152
<212> TYPE: PRT
<213> ORGANISM: Artificial Sequence
<220> FEATURE:
<223> OTHER INFORMATION: Affilin 161438

<400> SEQUENCE: 8

Met Gln Ile Phe Val Arg Thr His Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Ser Phe Ala
    50                  55                  60

His Arg Leu His Leu Val Leu Arg Leu Arg Ala Ala Met Gln Ile Phe
65                  70                  75                  80

Val Met Thr Arg Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150

<210> SEQ ID NO 9
<211> LENGTH: 152
<212> TYPE: PRT
<213> ORGANISM: Artificial Sequence
<220> FEATURE:
<223> OTHER INFORMATION: Affilin 164058

<400> SEQUENCE: 9

Met Gln Ile Phe Val Arg Thr Ile Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110
```

```
Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150

<210> SEQ ID NO 10
<211> LENGTH: 152
<212> TYPE: PRT
<213> ORGANISM: Artificial Sequence
<220> FEATURE:
<223> OTHER INFORMATION: Affilin 185036

<400> SEQUENCE: 10

Met Gln Ile Phe Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Leu Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Pro Ser Ile Leu His
    130                 135                 140

Leu Val Leu Arg Leu Arg Ala Ala
145                 150

<210> SEQ ID NO 11
<211> LENGTH: 152
<212> TYPE: PRT
<213> ORGANISM: Artificial Sequence
<220> FEATURE:
<223> OTHER INFORMATION: Affilin 192444

<400> SEQUENCE: 11

Met Gln Ile Phe Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Thr Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Leu Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110
```

-continued

```
Pro Pro Asp Gln Gln Arg Leu Ile Trp Ala Gly Thr Gln Leu Glu Asp
        115                 120                 125

Gly Arg Thr Leu Ser Asp Tyr Asn Ile Trp Thr Pro Ser Ile Leu His
        130                 135                 140

Leu Val Leu Arg Leu Arg Ala Ala
145                 150

<210> SEQ ID NO 12
<211> LENGTH: 152
<212> TYPE: PRT
<213> ORGANISM: Artificial Sequence
<220> FEATURE:
<223> OTHER INFORMATION: Affilin 191822

<400> SEQUENCE: 12

Met Gln Ile Phe Val Arg Thr Leu Thr Gly Gln Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Ala Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Leu Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Pro Ser Ile Leu His
        130                 135                 140

Leu Val Leu Arg Leu Arg Ala Ala
145                 150

<210> SEQ ID NO 13
<211> LENGTH: 152
<212> TYPE: PRT
<213> ORGANISM: Artificial Sequence
<220> FEATURE:
<223> OTHER INFORMATION: Affilin 185678

<400> SEQUENCE: 13

Met Gln Ile Phe Val Arg Thr Leu Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
```

-continued

```
            100             105             110

Pro Pro Asp Gln Gln Arg Leu Ile Trp Ala Gly Lys Gln Leu Glu Asp
        115             120             125

Gly Arg Thr Leu Ser Asp Tyr Asn Ile Gly His Glu Tyr Leu Leu His
    130             135             140

Leu Val Leu Arg Leu Arg Ala Ala
145             150

<210> SEQ ID NO 14
<211> LENGTH: 152
<212> TYPE: PRT
<213> ORGANISM: Artificial Sequence
<220> FEATURE:
<223> OTHER INFORMATION: Affilin 185152

<400> SEQUENCE: 14

Met Gln Ile Phe Val Arg Thr Met Thr Gly Lys Thr Ile Thr Leu Glu
1               5               10              15

Val Glu Pro Ser Asp Thr Ile Glu Asn Val Lys Ala Lys Ile Gln Asp
            20              25              30

Lys Glu Gly Ile Pro Pro Asp Gln Gln Arg Leu Ile Trp Ala Gly Lys
        35              40              45

Gln Leu Glu Asp Gly Arg Thr Leu Ser Asp Tyr Asn Ile Gly Phe Ala
    50              55              60

His Arg Leu His Leu Val Leu Arg Leu Arg Ala Ala Met Gln Ile Phe
65              70              75              80

Val Met Thr Gln Thr Gly Lys Thr Ile Thr Leu Glu Val Glu Pro Ser
                85              90              95

Asp Thr Ile Glu Asn Val Lys Ala Lys Ile Gln Asp Lys Glu Gly Ile
            100             105             110

Pro Pro Asp Gln Gln Arg Leu Ile Trp Ala Gly Lys Gln Leu Glu Asp
        115             120             125

Gly Arg Thr Leu Ser Asp Tyr Asn Ile Gly Asp Gly Asp Val Leu His
    130             135             140

Leu Val Leu Arg Leu Arg Ala Ala
145             150

<210> SEQ ID NO 15
<211> LENGTH: 152
<212> TYPE: PRT
<213> ORGANISM: Artificial Sequence
<220> FEATURE:
<223> OTHER INFORMATION: Affilin 164668   (164000)

<400> SEQUENCE: 15

Met Gln Ile Phe Val Arg Thr Met Thr Gly Lys Thr Ile Thr Leu Glu
1               5               10              15

Val Glu Pro Ser Asp Thr Ile Glu Asn Val Lys Ala Lys Ile Gln Asp
            20              25              30

Lys Glu Gly Ile Pro Pro Asp Gln Gln Arg Leu Ile Trp Ala Gly Lys
        35              40              45

Gln Leu Glu Asp Gly Arg Thr Leu Ser Asp Tyr Asn Ile Gly Phe Ala
    50              55              60

His Arg Leu His Leu Val Leu Arg Leu Arg Ala Ala Met Gln Ile Phe
65              70              75              80

Val Met Thr Gln Thr Gly Lys Thr Ile Thr Leu Glu Val Glu Pro Ser
                85              90              95
```

```
Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150
```

```
<210> SEQ ID NO 16
<211> LENGTH: 152
<212> TYPE: PRT
<213> ORGANISM: Artificial Sequence
<220> FEATURE:
<223> OTHER INFORMATION: Affilin 185071
```

```
<400> SEQUENCE: 16
```

```
Met Gln Ile Phe Val Arg Thr Met Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Trp Gly Gly
    50                  55                  60

His Arg Leu His Leu Val Leu Arg Leu Arg Ala Ala Met Gln Ile Phe
65                  70                  75                  80

Val Leu Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Pro Ser Ile Leu His
    130                 135                 140

Leu Val Leu Arg Leu Arg Ala Ala
145                 150
```

```
<210> SEQ ID NO 17
<211> LENGTH: 152
<212> TYPE: PRT
<213> ORGANISM: Artificial Sequence
<220> FEATURE:
<223> OTHER INFORMATION: Affilin 157424
```

```
<400> SEQUENCE: 17
```

```
Met Gln Ile Phe Val Arg Thr Pro Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Pro Ala
    50                  55                  60

His Gln Leu His Leu Val Leu Arg Leu Cys Ala Ala Met Gln Ile Phe
65                  70                  75                  80

Val Met Thr Gln Thr Gly Lys Thr Ile Thr Leu Glu Val Glu Pro Ser
                85                  90                  95
```

-continued

```
Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150
```

```
<210> SEQ ID NO 18
<211> LENGTH: 152
<212> TYPE: PRT
<213> ORGANISM: Artificial Sequence
<220> FEATURE:
<223> OTHER INFORMATION: Affilin 157423

<400> SEQUENCE: 18
```

```
Met Gln Ile Phe Val Arg Thr Pro Thr Gly Lys Thr Ile Thr Leu Glu
1                 5                 10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gln Pro Ala
    50                  55                  60

His Gln Leu His Leu Val Leu Arg Leu Arg Ala Ala Met Gln Ile Phe
65                  70                  75                  80

Val Met Thr Arg Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala
145                 150
```

```
<210> SEQ ID NO 19
<211> LENGTH: 152
<212> TYPE: PRT
<213> ORGANISM: Artificial Sequence
<220> FEATURE:
<223> OTHER INFORMATION: Affilin 161644

<400> SEQUENCE: 19
```

```
Met Gln Ile Phe Val Arg Thr Pro Thr Gly Lys Thr Ile Thr Leu Glu
1                 5                 10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Ser Tyr Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
```

```
                    85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
        130                 135                 140

Leu Val Leu Arg Leu Arg Ala Ala
145                 150

<210> SEQ ID NO 20
<211> LENGTH: 152
<212> TYPE: PRT
<213> ORGANISM: Artificial Sequence
<220> FEATURE:
<223> OTHER INFORMATION: Affilin 191829

<400> SEQUENCE: 20

Met Gln Ile Phe Val Arg Thr Gln Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Trp Ala
    50                  55                  60

His Arg Leu His Leu Val Leu Arg Leu Arg Ala Ala Met Gln Ile Phe
65                  70                  75                  80

Val Ala Thr Phe Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Pro Thr Ile Leu His
        130                 135                 140

Leu Val Leu Arg Leu Arg Ala Ala
145                 150

<210> SEQ ID NO 21
<211> LENGTH: 152
<212> TYPE: PRT
<213> ORGANISM: Artificial Sequence
<220> FEATURE:
<223> OTHER INFORMATION: Affilin 185113

<400> SEQUENCE: 21

Met Gln Ile Phe Val Arg Thr Trp Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80
```

-continued

```
Val Met Thr His Thr Gly Lys Thr Ile Thr Leu Glu Val Glu Pro Ser
            85              90              95

Asp Thr Ile Glu Asn Val Lys Ala Lys Ile Gln Asp Lys Glu Gly Ile
            100             105             110

Pro Pro Asp Gln Gln Arg Leu Ile Trp Ala Gly Lys Gln Leu Glu Asp
        115             120             125

Gly Arg Thr Leu Ser Asp Tyr Asn Ile Gly Asp Gly Asp Val Leu His
    130             135             140

Leu Val Leu Arg Leu Arg Ala Ala
145             150

<210> SEQ ID NO 22
<211> LENGTH: 152
<212> TYPE: PRT
<213> ORGANISM: Artificial Sequence
<220> FEATURE:
<223> OTHER INFORMATION: Affilin 185104

<400> SEQUENCE: 22

Met Gln Ile Phe Val Arg Thr Trp Thr Gly Lys Thr Ile Thr Leu Glu
1               5               10              15

Val Glu Pro Ser Asp Thr Ile Glu Asn Val Lys Ala Lys Ile Gln Asp
            20              25              30

Lys Glu Gly Ile Pro Pro Asp Gln Gln Arg Leu Ile Trp Ala Gly Lys
        35              40              45

Gln Leu Glu Asp Gly Arg Thr Leu Ser Asp Tyr Asn Ile Gly Phe Ala
    50              55              60

His Arg Leu His Leu Val Leu Arg Leu Arg Ala Ala Met Gln Ile Phe
65              70              75              80

Val Met Thr Gln Thr Gly Lys Thr Ile Thr Leu Glu Val Glu Pro Ser
            85              90              95

Asp Thr Ile Glu Asn Val Lys Ala Lys Ile Gln Asp Lys Glu Gly Ile
            100             105             110

Pro Pro Asp Gln Gln Arg Leu Ile Trp Ala Gly Lys Gln Leu Glu Asp
        115             120             125

Gly Arg Thr Leu Ser Asp Tyr Asn Ile Gly Asp Gly Asp Val Leu His
    130             135             140

Leu Val Leu Arg Leu Arg Ala Ala
145             150

<210> SEQ ID NO 23
<211> LENGTH: 152
<212> TYPE: PRT
<213> ORGANISM: Artificial Sequence
<220> FEATURE:
<223> OTHER INFORMATION: Affilin 162633

<400> SEQUENCE: 23

Met Gln Ile Phe Val Arg Thr Trp Thr Gly Lys Thr Ile Thr Leu Glu
1               5               10              15

Val Glu Pro Ser Asp Thr Ile Glu Asn Val Lys Ala Lys Ile Gln Asp
            20              25              30

Lys Glu Gly Ile Pro Pro Asp Gln Gln Arg Leu Ile Trp Ala Gly Lys
        35              40              45

Gln Leu Glu Asp Gly Arg Thr Leu Ser Asp Tyr Asn Ile Trp Trp Ala
    50              55              60

Asp Arg Leu His Leu Val Leu Arg Leu Arg Ala Ala Met Gln Ile Phe
65              70              75              80
```

-continued

```
Val Met Thr Gln Thr Gly Lys Thr Ile Thr Leu Glu Val Glu Pro Ser
             85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Trp Thr Thr Thr Phe Leu His
        130                 135                 140

Leu Val Leu Arg Leu Arg Ala Ala
145                 150

<210> SEQ ID NO 24
<211> LENGTH: 152
<212> TYPE: PRT
<213> ORGANISM: Artificial Sequence
<220> FEATURE:
<223> OTHER INFORMATION: Affilin 163970

<400> SEQUENCE: 24

Met Gln Ile Phe Val Trp Thr Pro Thr Gly Lys Thr Ile Thr Leu Glu
1               5                  10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
        50                  55                  60

His Leu Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
             85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Trp Thr Thr Thr Phe Leu His
        130                 135                 140

Leu Val Leu Arg Leu Arg Ala Ala
145                 150

<210> SEQ ID NO 25
<211> LENGTH: 82
<212> TYPE: PRT
<213> ORGANISM: Artificial Sequence
<220> FEATURE:
<223> OTHER INFORMATION: Affilin 164667 (161984)

<400> SEQUENCE: 25

Met Gln Ile Phe Val Lys Thr Leu Thr Phe Glu His Pro Ser Phe Gly
1               5                  10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln His
        35                  40                  45

Leu Tyr Trp Ala Gly Lys Gln Leu Glu Asp Gly Arg Thr Leu Ser Asp
        50                  55                  60

Tyr Asn Ile Lys His Asn Thr Trp Leu Glu Leu Met Leu Phe Leu Arg
```

-continued

```
65              70              75              80

Ala Ala

<210> SEQ ID NO 26
<211> LENGTH: 82
<212> TYPE: PRT
<213> ORGANISM: Artificial Sequence
<220> FEATURE:
<223> OTHER INFORMATION: Affilin 157434

<400> SEQUENCE: 26

Met Gln Ile Phe Val Lys Thr Leu Thr Asp Met Tyr Arg Phe Met Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln Ile
            35                  40                  45

Leu Trp Trp Ala Gly Lys Gln Leu Glu Asp Gly Arg Thr Leu Ser Asp
        50                  55                  60

Tyr Asn Ile Val Ala Tyr Arg Pro Leu Tyr Leu Thr Leu Ala Leu Arg
65                  70                  75                  80

Ala Ala

<210> SEQ ID NO 27
<211> LENGTH: 82
<212> TYPE: PRT
<213> ORGANISM: Artificial Sequence
<220> FEATURE:
<223> OTHER INFORMATION: Afffilin 161717

<400> SEQUENCE: 27

Met Gln Ile Phe Val Lys Thr Leu Thr Phe Glu His His Ser Phe Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln His
            35                  40                  45

Leu Tyr Trp Ala Gly Lys Gln Leu Glu Asp Gly Arg Thr Leu Ser Asp
        50                  55                  60

Tyr Asn Ile Lys His Asn Thr Trp Leu Glu Leu Met Leu Phe Leu Arg
65                  70                  75                  80

Ala Ala

<210> SEQ ID NO 28
<211> LENGTH: 82
<212> TYPE: PRT
<213> ORGANISM: Artificial Sequence
<220> FEATURE:
<223> OTHER INFORMATION: Affilin 161776

<400> SEQUENCE: 28

Met Gln Ile Phe Val Lys Thr Leu Thr Phe Glu His Lys Ser Phe Gly
1               5                   10                  15

Lys Thr Ile Thr Leu Glu Val Glu Pro Ser Asp Thr Ile Glu Asn Val
            20                  25                  30

Lys Ala Lys Ile Gln Asp Lys Glu Gly Ile Pro Pro Asp Gln Gln His
            35                  40                  45

Leu Tyr Trp Ala Gly Lys Gln Leu Glu Asp Gly Arg Thr Leu Ser Asp
        50                  55                  60
```

```
Tyr Asn Ile Lys His Asn Thr Trp Leu Glu Leu Met Leu Phe Leu Arg
65                  70                  75                  80

Ala Ala

<210> SEQ ID NO 29
<211> LENGTH: 82
<212> TYPE: PRT
<213> ORGANISM: Artificial Sequence
<220> FEATURE:
<223> OTHER INFORMATION: Affilin 162055

<400> SEQUENCE: 29

Met Gln Ile Phe Val Lys Thr Leu Thr Phe Glu His Asn Ser Phe Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45

Leu Tyr Trp Val Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala

<210> SEQ ID NO 30
<211> LENGTH: 82
<212> TYPE: PRT
<213> ORGANISM: Artificial Sequence
<220> FEATURE:
<223> OTHER INFORMATION: Affilin 162102

<400> SEQUENCE: 30

Met Gln Ile Phe Val Lys Thr Leu Thr Pro Ile Pro Pro Asp Trp Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45

Leu Tyr Trp Ala Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala

<210> SEQ ID NO 31
<211> LENGTH: 82
<212> TYPE: PRT
<213> ORGANISM: Artificial Sequence
<220> FEATURE:
<223> OTHER INFORMATION: Affilin 161912

<400> SEQUENCE: 31

Met Gln Ile Phe Val Lys Thr Leu Thr Pro Pro Phe Ala Phe Trp Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45
```

```
Leu Tyr Trp Ala Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala

<210> SEQ ID NO 32
<211> LENGTH: 82
<212> TYPE: PRT
<213> ORGANISM: Artificial Sequence
<220> FEATURE:
<223> OTHER INFORMATION: Affilin 162034

<400> SEQUENCE: 32

Met Gln Ile Phe Val Lys Thr Leu Thr Pro Gln Pro Pro Glu Phe Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45

Leu Tyr Trp Ala Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala

<210> SEQ ID NO 33
<211> LENGTH: 82
<212> TYPE: PRT
<213> ORGANISM: Artificial Sequence
<220> FEATURE:
<223> OTHER INFORMATION: Affilin 161843

<400> SEQUENCE: 33

Met Gln Ile Phe Val Lys Thr Leu Thr Pro Gln Pro Pro Glu Trp Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45

Leu Tyr Trp Ala Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala

<210> SEQ ID NO 34
<211> LENGTH: 82
<212> TYPE: PRT
<213> ORGANISM: Artificial Sequence
<220> FEATURE:
<223> OTHER INFORMATION: Affilin 161374

<400> SEQUENCE: 34

Met Gln Ile Phe Val Lys Thr Leu Thr Pro Gln Pro Pro Glu Tyr Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
```

```
                35                    40                    45

Leu Tyr Trp Ala Gly Lys Gln Leu Glu Asp Gly Arg Thr Leu Ser Asp
        50                    55                    60

Tyr Asn Ile Lys His Asn Thr Trp Leu Glu Leu Met Leu Phe Leu Arg
65                    70                    75                    80

Ala Ala
```

```
<210> SEQ ID NO 35
<211> LENGTH: 76
<212> TYPE: PRT
<213> ORGANISM: Artificial Sequence
<220> FEATURE:
<223> OTHER INFORMATION: Affilin 187093

<400> SEQUENCE: 35

Met Gln Ile Phe Val Trp Thr Arg Glu Phe Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75
```

```
<210> SEQ ID NO 36
<211> LENGTH: 76
<212> TYPE: PRT
<213> ORGANISM: Artificial Sequence
<220> FEATURE:
<223> OTHER INFORMATION: Affilin 187092

<400> SEQUENCE: 36

Met Gln Ile Phe Val Tyr Thr Ala Glu Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75
```

```
<210> SEQ ID NO 37
<211> LENGTH: 76
<212> TYPE: PRT
<213> ORGANISM: Artificial Sequence
<220> FEATURE:
<223> OTHER INFORMATION: Affilin 187064

<400> SEQUENCE: 37

Met Gln Ile Phe Val Tyr Thr Lys Gln Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45
```

```
Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75
```

```
<210> SEQ ID NO 38
<211> LENGTH: 76
<212> TYPE: PRT
<213> ORGANISM: Artificial Sequence
<220> FEATURE:
<223> OTHER INFORMATION: Affilin 187154

<400> SEQUENCE: 38
```

```
Met Gln Ile Phe Val Tyr Thr Arg Ala Leu Lys Gln Ile Thr Leu Glu
1               5                   10                  15

Val Gly Pro Ser Asp Thr Ile Glu Asn Val Lys Ala Lys Ile Arg Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asp Leu Asp Leu Arg Ala Ala
65                  70                  75
```

```
<210> SEQ ID NO 39
<211> LENGTH: 76
<212> TYPE: PRT
<213> ORGANISM: Artificial Sequence
<220> FEATURE:
<223> OTHER INFORMATION: Affilin 187165

<400> SEQUENCE: 39
```

```
Met Gln Ile Phe Val Tyr Thr Arg Ala Leu Lys Gln Ile Thr Leu Glu
1               5                   10                  15

Val Glu Pro Ser Asp Thr Val Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asp Leu Asp Leu Arg Ala Ala
65                  70                  75
```

```
<210> SEQ ID NO 40
<211> LENGTH: 76
<212> TYPE: PRT
<213> ORGANISM: Artificial Sequence
<220> FEATURE:
<223> OTHER INFORMATION: Affilin 187191

<400> SEQUENCE: 40
```

```
Met Gln Ile Phe Val Tyr Thr Arg Ala Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Arg
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
```

```
65                  70                  75

<210> SEQ ID NO 41
<211> LENGTH: 76
<212> TYPE: PRT
<213> ORGANISM: Artificial Sequence
<220> FEATURE:
<223> OTHER INFORMATION: Affilin 187210

<400> SEQUENCE: 41

Met Gln Ile Phe Val Tyr Thr Arg Ala Leu Lys Gln Ile Thr Leu Glu
1               5                   10                  15

Val Glu Pro Ser Asp Thr Ile Glu Asn Val Lys Ala Lys Ile Gln Asp
            20                  25                  30

Arg Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 42
<211> LENGTH: 76
<212> TYPE: PRT
<213> ORGANISM: Artificial Sequence
<220> FEATURE:
<223> OTHER INFORMATION: Affilin 187131

<400> SEQUENCE: 42

Met Gln Ile Phe Val Tyr Thr Arg Ala Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Gly Leu Arg Ala Ala
65                  70                  75

<210> SEQ ID NO 43
<211> LENGTH: 76
<212> TYPE: PRT
<213> ORGANISM: Artificial Sequence
<220> FEATURE:
<223> OTHER INFORMATION: Affilin 187170

<400> SEQUENCE: 43

Met Gln Ile Phe Val Tyr Thr Arg Ala Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asn Leu Arg Ala Ala
65                  70                  75

<210> SEQ ID NO 44
```

```
<211> LENGTH: 76
<212> TYPE: PRT
<213> ORGANISM: Artificial Sequence
<220> FEATURE:
<223> OTHER INFORMATION: Affilin 187096

<400> SEQUENCE: 44

Met Gln Ile Phe Val Tyr Thr Arg Glu Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 45
<211> LENGTH: 76
<212> TYPE: PRT
<213> ORGANISM: Artificial Sequence
<220> FEATURE:
<223> OTHER INFORMATION: Affilin 181514

<400> SEQUENCE: 45

Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Lys Leu Lys Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 46
<211> LENGTH: 76
<212> TYPE: PRT
<213> ORGANISM: Artificial Sequence
<220> FEATURE:
<223> OTHER INFORMATION: Affilin 181515

<400> SEQUENCE: 46

Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 47
<211> LENGTH: 76
<212> TYPE: PRT
<213> ORGANISM: Artificial Sequence
<220> FEATURE:
```

<223> OTHER INFORMATION: Affilin 187134

<400> SEQUENCE: 47

Met Gln Ile Phe Val Tyr Thr Arg Val Leu Lys Gln Ile Thr Leu Ala
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 48
<211> LENGTH: 76
<212> TYPE: PRT
<213> ORGANISM: Artificial Sequence
<220> FEATURE:
<223> OTHER INFORMATION: Affilin 187186

<400> SEQUENCE: 48

Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Arg Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75

<210> SEQ ID NO 49
<211> LENGTH: 76
<212> TYPE: PRT
<213> ORGANISM: Artificial Sequence
<220> FEATURE:
<223> OTHER INFORMATION: Affilin 187283

<400> SEQUENCE: 49

Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Arg Asp Leu Arg Ala Ala
65                  70                  75

<210> SEQ ID NO 50
<211> LENGTH: 76
<212> TYPE: PRT
<213> ORGANISM: Artificial Sequence
<220> FEATURE:
<223> OTHER INFORMATION: Affilin 187295

<400> SEQUENCE: 50

```
Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Met Leu Phe Trp Lys Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Arg Arg Ala Ala
65                  70                  75
```

<210> SEQ ID NO 51
<211> LENGTH: 76
<212> TYPE: PRT
<213> ORGANISM: Artificial Sequence
<220> FEATURE:
<223> OTHER INFORMATION: Affilin 187178

<400> SEQUENCE: 51

```
Met Gln Ile Phe Val Tyr Thr Arg Val Leu Lys Gln Ile Thr Leu Glu
1               5                   10                  15

Val Glu Pro Ser Asp Thr Ile Glu Asn Val Lys Ala Lys Ile Gln Asp
            20                  25                  30

Lys Glu Gly Thr Pro Pro Asp Gln Gln Thr Leu Phe Trp Arg Gly Lys
        35                  40                  45

Gln Leu Glu Asp Gly Arg Thr Leu Ser Asp Tyr Asn Ile Trp Trp Asn
    50                  55                  60

Pro Asn Leu Ser Leu Asn Leu Asp Leu Arg Ala Ala
65                  70                  75
```

<210> SEQ ID NO 52
<211> LENGTH: 404
<212> TYPE: PRT
<213> ORGANISM: Artificial Sequence
<220> FEATURE:
<223> OTHER INFORMATION: homodimer of 167528 (162462)

<400> SEQUENCE: 52

```
Met Gln Ile Phe Val Arg Thr Pro Thr Gly Lys Thr Ile Thr Leu Glu
1               5                   10                  15

Val Glu Pro Ser Asp Thr Ile Glu Asn Val Lys Ala Lys Ile Gln Asp
            20                  25                  30

Lys Glu Gly Ile Pro Pro Asp Gln Gln Arg Leu Ile Trp Ala Gly Lys
        35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
            85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
            115                 120                 125

Gly Arg Thr Leu Ser Asp Tyr Asn Ile Trp Thr Thr Thr Phe Leu His
        130                 135                 140

Leu Val Leu Arg Leu Arg Ala Ala Ser Ala Pro Ala Ala Ser Pro Ser
145                 150                 155                 160
```

-continued

Pro Ala Ala Pro Ala Pro Ser Pro Ala Ser Pro Ala Pro Ala Ser Pro
                165             170             175

Ala Ser Ala Pro Ser Ala Pro Ala Ser Ala Pro Pro Ala Ala Ser Ala
                180             185             190

Met Gln Ile Phe Val Arg Thr Pro Thr Gly Lys Thr Ile Thr Leu Glu
                195             200             205

Val Glu Pro Ser Asp Thr Ile Glu Asn Val Lys Ala Lys Ile Gln Asp
        210             215             220

Lys Glu Gly Ile Pro Pro Asp Gln Gln Arg Leu Ile Trp Ala Gly Lys
225             230             235             240

Gln Leu Glu Asp Gly Arg Thr Leu Ser Asp Tyr Asn Ile Gly Phe Ala
                245             250             255

His Arg Leu His Leu Val Leu Arg Leu Arg Ala Ala Met Gln Ile Phe
                260             265             270

Val Met Thr Gln Thr Gly Lys Thr Ile Thr Leu Glu Val Glu Pro Ser
        275             280             285

Asp Thr Ile Glu Asn Val Lys Ala Lys Ile Gln Asp Lys Glu Gly Ile
        290             295             300

Pro Pro Asp Gln Gln Arg Leu Ile Trp Ala Gly Lys Gln Leu Glu Asp
305             310             315             320

Gly Arg Thr Leu Ser Asp Tyr Asn Ile Trp Thr Thr Thr Phe Leu His
                325             330             335

Leu Val Leu Arg Leu Arg Ala Ala Ser Ala Pro Ala Pro Ser Ala Pro
                340             345             350

Ala Ala Ser Ala Pro Pro Ala Pro Ala Ala Pro Cys Ala Pro Ala Ala
                355             360             365

Pro Ala Ser Ala Pro Ala Pro Ala Ser Ala Pro Ala Ala Ser Pro Cys
        370             375             380

Pro Ala Ala Pro Ala Pro Ser Pro Ala Ser Pro Ala Pro Ala Ser Pro
385             390             395             400

Ala Ser Ala Pro

<210> SEQ ID NO 53
<211> LENGTH: 264
<212> TYPE: PRT
<213> ORGANISM: Artificial Sequence
<220> FEATURE:
<223> OTHER INFORMATION: homomer 161984 (164661)

<400> SEQUENCE: 53

Met Gln Ile Phe Val Lys Thr Leu Thr Phe Glu His Pro Ser Phe Gly
1               5               10              15

Lys Thr Ile Thr Leu Glu Val Glu Pro Ser Asp Thr Ile Glu Asn Val
                20              25              30

Lys Ala Lys Ile Gln Asp Lys Glu Gly Ile Pro Pro Asp Gln Gln His
        35              40              45

Leu Tyr Trp Ala Gly Lys Gln Leu Glu Asp Gly Arg Thr Leu Ser Asp
        50              55              60

Tyr Asn Ile Lys His Asn Thr Trp Leu Glu Leu Met Leu Phe Leu Arg
65              70              75              80

Ala Ala Ser Ala Pro Ala Ala Ser Pro Ser Pro Ala Ala Pro Ala Pro
                85              90              95

Ser Pro Ala Ser Pro Ala Pro Ala Ser Pro Ala Ser Ala Pro Ser Ala
                100             105             110

-continued

```
Pro Ala Ser Ala Pro Pro Ala Ala Ser Ala Met Gln Ile Phe Val Lys
        115                 120                 125

Thr Leu Thr Phe Glu His Pro Ser Phe Gly Lys Thr Ile Thr Leu Glu
        130                 135                 140

Val Glu Pro Ser Asp Thr Ile Glu Asn Val Lys Ala Lys Ile Gln Asp
145                 150                 155                 160

Lys Glu Gly Ile Pro Pro Asp Gln Gln His Leu Tyr Trp Ala Gly Lys
                165                 170                 175

Gln Leu Glu Asp Gly Arg Thr Leu Ser Asp Tyr Asn Ile Lys His Asn
        180                 185                 190

Thr Trp Leu Glu Leu Met Leu Phe Leu Arg Ala Ala Ser Ala Pro Ala
        195                 200                 205

Pro Ser Ala Pro Ala Ala Ser Ala Pro Pro Ala Pro Ala Ala Pro Cys
        210                 215                 220

Ala Pro Ala Ala Pro Ala Ser Ala Pro Ala Pro Ala Ser Ala Pro Ala
225                 230                 235                 240

Ala Ser Pro Cys Pro Ala Ala Pro Ala Pro Ser Pro Ala Ser Pro Ala
                245                 250                 255

Pro Ala Ser Pro Ala Ser Ala Pro
                260
```

```
<210> SEQ ID NO 54
<211> LENGTH: 334
<212> TYPE: PRT
<213> ORGANISM: Artificial Sequence
<220> FEATURE:
<223> OTHER INFORMATION: heterodimer 42 of 161984 und 162462 (CID167526)

<400> SEQUENCE: 54
```

```
Met Gln Ile Phe Val Lys Thr Leu Thr Phe Glu His Pro Ser Phe Gly
1               5                   10                  15

Lys Thr Ile Thr Leu Glu Val Glu Pro Ser Asp Thr Ile Glu Asn Val
                20                  25                  30

Lys Ala Lys Ile Gln Asp Lys Glu Gly Ile Pro Pro Asp Gln Gln His
        35                  40                  45

Leu Tyr Trp Ala Gly Lys Gln Leu Glu Asp Gly Arg Thr Leu Ser Asp
    50                  55                  60

Tyr Asn Ile Lys His Asn Thr Trp Leu Glu Leu Met Leu Phe Leu Arg
65                  70                  75                  80

Ala Ala Ser Ala Pro Ala Ala Ser Pro Ser Pro Ala Ala Pro Ala Pro
                85                  90                  95

Ser Pro Ala Ser Pro Ala Pro Ala Ser Pro Ala Ser Ala Pro Ser Ala
                100                 105                 110

Pro Ala Ser Ala Pro Pro Ala Ala Ser Ala Met Gln Ile Phe Val Arg
        115                 120                 125

Thr Pro Thr Gly Lys Thr Ile Thr Leu Glu Val Glu Pro Ser Asp Thr
        130                 135                 140

Ile Glu Asn Val Lys Ala Lys Ile Gln Asp Lys Glu Gly Ile Pro Pro
145                 150                 155                 160

Asp Gln Gln Arg Leu Ile Trp Ala Gly Lys Gln Leu Glu Asp Gly Arg
                165                 170                 175

Thr Leu Ser Asp Tyr Asn Ile Gly Phe Ala His Arg Leu His Leu Val
                180                 185                 190

Leu Arg Leu Arg Ala Ala Met Gln Ile Phe Val Met Thr Gln Thr Gly
        195                 200                 205
```

-continued

```
Lys Thr Ile Thr Leu Glu Val Glu Pro Ser Asp Thr Ile Glu Asn Val
    210                 215                 220

Lys Ala Lys Ile Gln Asp Lys Glu Gly Ile Pro Pro Asp Gln Gln Arg
225                 230                 235                 240

Leu Ile Trp Ala Gly Lys Gln Leu Glu Asp Gly Arg Thr Leu Ser Asp
                245                 250                 255

Tyr Asn Ile Trp Thr Thr Thr Phe Leu His Leu Val Leu Arg Leu Arg
                260                 265                 270

Ala Ala Ser Ala Pro Ala Pro Ser Ala Pro Ala Ala Ser Ala Pro Pro
                275                 280                 285

Ala Pro Ala Ala Pro Cys Ala Pro Ala Ala Pro Ala Ser Ala Pro Ala
    290                 295                 300

Pro Ala Ser Ala Pro Ala Ala Ser Pro Cys Pro Ala Ala Pro Ala Pro
305                 310                 315                 320

Ser Pro Ala Ser Pro Ala Pro Ala Ser Pro Ala Ser Ala Pro
                325                 330
```

<210> SEQ ID NO 55
<211> LENGTH: 334
<212> TYPE: PRT
<213> ORGANISM: Artificial Sequence
<220> FEATURE:
<223> OTHER INFORMATION: heterodimer 24 162462 und 161984 (CID167525)

<400> SEQUENCE: 55

```
Met Gln Ile Phe Val Arg Thr Pro Thr Gly Lys Thr Ile Thr Leu Glu
1               5                   10                  15

Val Glu Pro Ser Asp Thr Ile Glu Asn Val Lys Ala Lys Ile Gln Asp
                20                  25                  30

Lys Glu Gly Ile Pro Pro Asp Gln Gln Arg Leu Ile Trp Ala Gly Lys
            35                  40                  45

Gln Leu Glu Asp Gly Arg Thr Leu Ser Asp Tyr Asn Ile Gly Phe Ala
    50                  55                  60

His Arg Leu His Leu Val Leu Arg Leu Arg Ala Ala Met Gln Ile Phe
65                  70                  75                  80

Val Met Thr Gln Thr Gly Lys Thr Ile Thr Leu Glu Val Glu Pro Ser
                85                  90                  95

Asp Thr Ile Glu Asn Val Lys Ala Lys Ile Gln Asp Lys Glu Gly Ile
            100                 105                 110

Pro Pro Asp Gln Gln Arg Leu Ile Trp Ala Gly Lys Gln Leu Glu Asp
        115                 120                 125

Gly Arg Thr Leu Ser Asp Tyr Asn Ile Trp Thr Thr Thr Phe Leu His
    130                 135                 140

Leu Val Leu Arg Leu Arg Ala Ala Ser Ala Pro Ala Ala Ser Pro Ser
145                 150                 155                 160

Pro Ala Ala Pro Ala Pro Ser Pro Ala Ser Pro Ala Pro Ala Ser Pro
                165                 170                 175

Ala Ser Ala Pro Ser Ala Pro Ala Ser Ala Pro Pro Ala Ala Ser Ala
            180                 185                 190

Met Gln Ile Phe Val Lys Thr Leu Thr Phe Glu His Pro Ser Phe Gly
        195                 200                 205

Lys Thr Ile Thr Leu Glu Val Glu Pro Ser Asp Thr Ile Glu Asn Val
    210                 215                 220

Lys Ala Lys Ile Gln Asp Lys Glu Gly Ile Pro Pro Asp Gln Gln His
225                 230                 235                 240
```

-continued

```
Leu Tyr Trp Ala Gly Lys Gln Leu Glu Asp Gly Arg Thr Leu Ser Asp
                245                 250                 255

Tyr Asn Ile Lys His Asn Thr Trp Leu Glu Leu Met Leu Phe Leu Arg
            260                 265                 270

Ala Ala Ser Ala Pro Ala Pro Ser Ala Pro Ala Ala Ser Ala Pro Pro
            275                 280                 285

Ala Pro Ala Ala Pro Cys Ala Pro Ala Ala Pro Ala Ser Ala Pro Ala
    290                 295                 300

Pro Ala Ser Ala Pro Ala Ala Ser Pro Cys Pro Ala Ala Pro Ala Pro
305                 310                 315                 320

Ser Pro Ala Ser Pro Ala Pro Ala Ser Pro Ala Ser Ala Pro
                325                 330
```

```
<210> SEQ ID NO 56
<211> LENGTH: 5
<212> TYPE: PRT
<213> ORGANISM: Artificial Sequence
<220> FEATURE:
<223> OTHER INFORMATION: motif

<400> SEQUENCE: 56

Gly Phe Ala His Arg
1               5

<210> SEQ ID NO 57
<211> LENGTH: 5
<212> TYPE: PRT
<213> ORGANISM: Artificial Sequence
<220> FEATURE:
<223> OTHER INFORMATION: motif

<400> SEQUENCE: 57

Gly Trp Ala His Arg
1               5

<210> SEQ ID NO 58
<211> LENGTH: 5
<212> TYPE: PRT
<213> ORGANISM: Artificial Sequence
<220> FEATURE:
<223> OTHER INFORMATION: motif

<400> SEQUENCE: 58

Trp Thr Thr Thr Phe
1               5

<210> SEQ ID NO 59
<211> LENGTH: 5
<212> TYPE: PRT
<213> ORGANISM: Artificial Sequence
<220> FEATURE:
<223> OTHER INFORMATION: motif

<400> SEQUENCE: 59

Lys His Asn Thr Trp
1               5

<210> SEQ ID NO 60
<211> LENGTH: 5
<212> TYPE: PRT
<213> ORGANISM: Artificial Sequence
<220> FEATURE:
<223> OTHER INFORMATION: motif

<400> SEQUENCE: 60
```

```
Val Ala Tyr Arg Pro
1               5

<210> SEQ ID NO 61
<211> LENGTH: 5
<212> TYPE: PRT
<213> ORGANISM: Artificial Sequence
<220> FEATURE:
<223> OTHER INFORMATION: motfi

<400> SEQUENCE: 61

Trp Trp Asn Pro Asn
1               5

<210> SEQ ID NO 62
<211> LENGTH: 40
<212> TYPE: PRT
<213> ORGANISM: Artificial Sequence
<220> FEATURE:
<223> OTHER INFORMATION: linker

<400> SEQUENCE: 62

Ser Ala Pro Ala Ala Ser Pro Ser Pro Ala Ala Pro Ala Pro Ser Pro
1               5                   10                  15

Ala Ser Pro Ala Pro Ala Ser Pro Ala Ser Ala Pro Ser Ala Pro Ala
            20                  25                  30

Ser Ala Pro Pro Ala Ala Ser Ala
        35                  40

<210> SEQ ID NO 63
<211> LENGTH: 21
<212> TYPE: PRT
<213> ORGANISM: Artificial Sequence
<220> FEATURE:
<223> OTHER INFORMATION: linker

<400> SEQUENCE: 63

Pro Ala Ala Pro Ala Pro Ser Pro Ala Ser Pro Ala Pro Ala Ser Pro
1               5                   10                  15

Ala Ser Ala Pro Ser
            20

<210> SEQ ID NO 64
<211> LENGTH: 61
<212> TYPE: PRT
<213> ORGANISM: Artificial Sequence
<220> FEATURE:
<223> OTHER INFORMATION: coupling domain

<400> SEQUENCE: 64

Ser Ala Pro Ala Pro Ser Ala Pro Ala Ala Ser Ala Pro Pro Ala Pro
1               5                   10                  15

Ala Ala Pro Cys Ala Pro Ala Ala Pro Ala Ser Ala Pro Ala Pro Ala
            20                  25                  30

Ser Ala Pro Ala Ala Ser Pro Cys Pro Ala Ala Pro Ala Pro Ser Pro
        35                  40                  45

Ala Ser Pro Ala Pro Ala Ser Pro Ala Ser Ala Pro Ser
    50                  55                  60

<210> SEQ ID NO 65
<211> LENGTH: 40
<212> TYPE: PRT
<213> ORGANISM: Artificial Sequence
```

```
<220> FEATURE:
<223> OTHER INFORMATION: coupling domain

<400> SEQUENCE: 65

Ser Ala Pro Ala Pro Ser Ala Pro Ala Ala Ser Ala Pro Pro Ala Pro
1               5                   10                  15

Ala Ala Pro Cys Ala Pro Ala Ala Pro Ala Ser Ala Pro Ala Pro Ala
            20                  25                  30

Ser Ala Pro Ala Ala Ser Pro Cys
        35                  40

<210> SEQ ID NO 66
<211> LENGTH: 20
<212> TYPE: PRT
<213> ORGANISM: Artificial Sequence
<220> FEATURE:
<223> OTHER INFORMATION: coupling domain

<400> SEQUENCE: 66

Ser Ala Pro Ala Pro Ser Ala Pro Ala Ala Ser Ala Pro Pro Ala Pro
1               5                   10                  15

Ala Ala Pro Cys
            20

<210> SEQ ID NO 67
<211> LENGTH: 20
<212> TYPE: PRT
<213> ORGANISM: Artificial Sequence
<220> FEATURE:
<223> OTHER INFORMATION: coupling domain

<400> SEQUENCE: 67

Ala Pro Ala Ala Pro Ala Ser Ala Pro Ala Pro Ala Ser Ala Pro Ala
1               5                   10                  15

Ala Ser Pro Cys
            20

<210> SEQ ID NO 68
<211> LENGTH: 33
<212> TYPE: PRT
<213> ORGANISM: Artificial Sequence
<220> FEATURE:
<223> OTHER INFORMATION: coupling domain

<400> SEQUENCE: 68

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
            20                  25                  30

Cys

<210> SEQ ID NO 69
<211> LENGTH: 33
<212> TYPE: PRT
<213> ORGANISM: Artificial Sequence
<220> FEATURE:
<223> OTHER INFORMATION: coupling domain

<400> SEQUENCE: 69

Ala Pro Ala Ala Ser Pro Ser Pro Ala Ala Pro Ala Pro Ser Pro Ala
1               5                   10                  15

Ser Pro Ala Pro Ala Ser Pro Ala Ser Ala Pro Ser Ala Pro Ala Ser
            20                  25                  30
```

Cys

<210> SEQ ID NO 70
<211> LENGTH: 98
<212> TYPE: PRT
<213> ORGANISM: Artificial Sequence
<220> FEATURE:
<223> OTHER INFORMATION: coupling domain

<400> SEQUENCE: 70

Ser Ala Pro Ala Pro Ser Ala Pro Ala Ala Ser Ala Pro Pro Ala Pro
1               5                   10                  15

Ala Ala Pro Ala Ala Pro Ala Ala Pro Ala Ser Ala Pro Ala Pro Ala
            20                  25                  30

Pro Ala Pro Ala Ala Ser Pro Ser Pro Ala Ala Pro Ala Pro Ser Pro
        35                  40                  45

Ala Ala Pro Ala Pro Ala Ser Pro Ala Ser Ala Pro Ser Ala Pro Ala
    50                  55                  60

Ser Ala Pro Pro Ala Ala Pro Ser Ala Ala Ala Ser Pro Ala Pro Ser
65                  70                  75                  80

Ala Pro Ala Pro Ala Ala Ser Pro Ala Ala Ala Pro Ala Ser Ala Ala
                85                  90                  95

Pro Ala

<210> SEQ ID NO 71
<211> LENGTH: 10
<212> TYPE: PRT
<213> ORGANISM: Artificial Sequence
<220> FEATURE:
<223> OTHER INFORMATION: strep

<400> SEQUENCE: 71

Ser Ala Trp Ser His Pro Gln Phe Glu Lys
1               5                   10

<210> SEQ ID NO 72
<211> LENGTH: 5
<212> TYPE: PRT
<213> ORGANISM: Artificial Sequence
<220> FEATURE:
<223> OTHER INFORMATION: motif

<400> SEQUENCE: 72

Ser Phe Ala His Arg
1               5

<210> SEQ ID NO 73
<211> LENGTH: 5
<212> TYPE: PRT
<213> ORGANISM: Artificial Sequence
<220> FEATURE:
<223> OTHER INFORMATION: motif

<400> SEQUENCE: 73

Ser Tyr Ala His Arg
1               5

<210> SEQ ID NO 74
<211> LENGTH: 5
<212> TYPE: PRT
<213> ORGANISM: Artificial Sequence
<220> FEATURE:
<223> OTHER INFORMATION: motif

```
<400> SEQUENCE: 74

Gly Phe Ala His Leu
1               5

<210> SEQ ID NO 75
<211> LENGTH: 5
<212> TYPE: PRT
<213> ORGANISM: Artificial Sequence
<220> FEATURE:
<223> OTHER INFORMATION: motif

<400> SEQUENCE: 75

Trp Thr Pro Ser Ile
1               5

<210> SEQ ID NO 76
<211> LENGTH: 5
<212> TYPE: PRT
<213> ORGANISM: Artificial Sequence
<220> FEATURE:
<223> OTHER INFORMATION: motif

<400> SEQUENCE: 76

Trp Thr Glu Thr Ile
1               5

<210> SEQ ID NO 77
<211> LENGTH: 5
<212> TYPE: PRT
<213> ORGANISM: Artificial Sequence
<220> FEATURE:
<223> OTHER INFORMATION: motif

<400> SEQUENCE: 77

Gly Asp Gly Asp Val
1               5

<210> SEQ ID NO 78
<211> LENGTH: 8
<212> TYPE: PRT
<213> ORGANISM: Artificial Sequence
<220> FEATURE:
<223> OTHER INFORMATION: FlagTag

<400> SEQUENCE: 78

Asp Tyr Lys Asp Asp Asp Asp Lys
1               5

<210> SEQ ID NO 79
<211> LENGTH: 5
<212> TYPE: PRT
<213> ORGANISM: Artificial Sequence
<220> FEATURE:
<223> OTHER INFORMATION: motif

<400> SEQUENCE: 79

Gly His Glu Tyr Leu
1               5

<210> SEQ ID NO 80
<211> LENGTH: 5
<212> TYPE: PRT
<213> ORGANISM: Artificial Sequence
<220> FEATURE:
<223> OTHER INFORMATION: motif
```

```
<400> SEQUENCE: 80

Trp Thr Pro Thr Ile
1               5

<210> SEQ ID NO 81
<211> LENGTH: 6
<212> TYPE: PRT
<213> ORGANISM: Artificial Sequence
<220> FEATURE:
<223> OTHER INFORMATION: motif
<220> FEATURE:
<221> NAME/KEY: Xaa
<222> LOCATION: (4)..(4)
<223> OTHER INFORMATION: can be any amino acid, preferably P, H, K, or N

<400> SEQUENCE: 81

Phe Glu His Xaa Ser Phe
1               5

<210> SEQ ID NO 82
<211> LENGTH: 6
<212> TYPE: PRT
<213> ORGANISM: Artificial Sequence
<220> FEATURE:
<223> OTHER INFORMATION: motif
<220> FEATURE:
<221> NAME/KEY: Xaa
<222> LOCATION: (6)..(6)
<223> OTHER INFORMATION: Xaa can be W, F, or Y

<400> SEQUENCE: 82

Pro Gln Pro Pro Glu Xaa
1               5

<210> SEQ ID NO 83
<211> LENGTH: 6
<212> TYPE: PRT
<213> ORGANISM: Artificial Sequence
<220> FEATURE:
<223> OTHER INFORMATION: motif

<400> SEQUENCE: 83

Pro Pro Phe Ala Phe Trp
1               5

<210> SEQ ID NO 84
<211> LENGTH: 6
<212> TYPE: PRT
<213> ORGANISM: Artificial Sequence
<220> FEATURE:
<223> OTHER INFORMATION: motif

<400> SEQUENCE: 84

Pro Ile Pro Pro Asp Trp
1               5

<210> SEQ ID NO 85
<211> LENGTH: 6
<212> TYPE: PRT
<213> ORGANISM: Artificial Sequence
<220> FEATURE:
<223> OTHER INFORMATION: motif

<400> SEQUENCE: 85

Asp Met Tyr Arg Phe Met
1               5
```

-continued

```
<210> SEQ ID NO 86
<211> LENGTH: 5
<212> TYPE: PRT
<213> ORGANISM: Artificial Sequence
<220> FEATURE:
<223> OTHER INFORMATION: motif
<220> FEATURE:
<221> NAME/KEY: Xaa
<222> LOCATION: (2)..(2)
<223> OTHER INFORMATION: Xaa is an aromatic amino acid, preferably F or
      W

<400> SEQUENCE: 86

Gly Xaa Ala His Arg
1               5
```

PSMA SPECIFIC BINDING PROTEINS FOR CANCER DIAGNOSIS AND TREATMENT

FIELD OF THE INVENTION

The present invention relates to new binding proteins that are specific for prostate specific membrane antigen (PSMA). The invention further refers to PSMA binding proteins that further comprise a diagnostically or therapeutically active component. Further aspects of the invention cover the use of these PSMA binding proteins in medicine, for example, in diagnosis and therapy of cancer associated with PSMA expression.

BACKGROUND OF THE INVENTION

The prostate specific membrane antigen (PSMA) is expressed in tumors, particularly in prostate cancer. Overexpression of PSMA has also been shown in the neovasculature of other solid tumors for example in breast, kidney, lung, ovarian, colorectal, bladder, gastric or brain cancers (e.g. glioblastoma), and multiple myeloma. It increases with progression of the cancer with particular high levels in metastatic disease. The three-domain glycoprotein (extracellular, transmembrane, and short intracellular domain) is mediating tumor nutrition and cell proliferation. Targeted PSMA specific monoclonal antibodies were developed for diagnosis and treatment of cancer, in particular prostate cancer. So far, the only approved agent for diagnostic imaging and staining of newly diagnosed and recurrent prostate cancer patients is a radiolabeled murine monoclonal antibody Capromab Pendetide. However, the antibody is not of therapeutic benefit due to the binding to an intracellular epitope of PSMA. Second generation monoclonal antibodies binding to extracellular epitopes of PSMA were developed such as murine monoclonal antibody J591. J591 was tested for in vivo imaging of progressive solid tumors or for capturing of metastatic circulating tumor cells. Its therapeutic use is confined by toxic side effects and short serum half-lives.

PSMA-specific monoclonal antibodies as agents for diagnostic and therapeutic approaches, for example for PSMA-radioimmunotherapy and PSMA-radioimaging, have further major disadvantages. One is the complex molecular structure and the corresponding complicated production process. The other is their large size, resulting in poor tissue penetration in vivo. In combination with long circulation times antibody based compounds for imaging applications may result in poor contrast due to a high background signal.

Further, the frequent development of resistance to initially effective treatments constitutes a need for additional and improved therapeutics for prostate cancer and other cancers overexpressing PSMA.

Diagnosis and treatment of PSMA related cancer is not adequately addressed by existing options, and as a consequence, many patients do not adequately benefit from current strategies. Needless to say that there is a strong need for novel strategies for diagnosis and treatment of PSMA related tumors.

One objective of the present invention is the provision of molecules for specific targeting of PSMA for allowing targeted diagnostic and treatment options, including detection of PSMA positive tumors. Targeting this tumor-associated protein may offer benefit to patients with unmet need for novel diagnostic and therapeutic routes. Targeting PSMA suggests potentially non-toxic diagnostic and treatment approach, due to low and restricted distribution of PSMA in normal tissues. Thus, binding proteins with specificity for PSMA may enable effective medical options for cancer, and finally improve quality of life for patients.

The invention provides novel PSMA binding molecules for new and improved strategies in the diagnosis and treatment of PSMA related cancer.

The above-described objectives and advantages are achieved by the subject-matters of the enclosed claims. The present invention meets the needs presented above by providing examples for PSMA binding proteins. The above overview does not necessarily describe all problems solved by the present invention.

SUMMARY OF THE INVENTION

The present disclosure provides the following [1] to [15], without being specifically limited thereto:

[1] A prostate specific membrane antigen (PSMA) binding protein, comprising at least one amino acid binding motif selected from GFAHR (SEQ ID NO: 56), GWAHR (SEQ ID NO: 57), SFAHR (SEQ ID NO: 72), SYAHR (SEQ ID NO: 73), GFAHL (SEQ ID NO: 74), WTTTF (SEQ ID NO: 58), WTPSI (SEQ ID NO: 75), WTETI (SEQ ID NO: 76), GHEYL (SEQ ID NO: 79), GDGDV (SEQ ID NO: 77), KHNTW (SEQ ID NO: 59), VAYRP (SEQ ID NO: 60), or WWNPN (SEQ ID NO: 61), or motifs with 80% identity thereto.

[2] The PSMA binding protein according to [1], comprising one or more ubiquitin mutein(s) based on ubiquitin according to SEQ ID NO: 1.

[3] The PSMA binding protein according to [2], wherein the amino acid residues of binding motif correspond to positions 62, 63, 64, 65, 66 of ubiquitin according to SEQ ID NO: 1, preferably the PSMA binding protein, comprising one or more ubiquitin mutein(s) based on ubiquitin according to SEQ ID NO: 1 and comprising an amino acid binding motif GFAHR (SEQ ID NO: 56), or a motif with 80% identity thereto, at amino acid residues that correspond to positions 62, 63, 64, 65, 66 of ubiquitin according to SEQ ID NO: 1.

[4] The PSMA binding protein according to [3], wherein additionally amino acids corresponding to positions 6 and 8 of ubiquitin of SEQ ID NO: 1 are substituted.

[5] The PSMA binding protein according to [3], wherein additionally amino acids corresponding to positions 42, 44, 68, 70, and 72 of ubiquitin of SEQ ID NO: 1 are substituted.

[6] The PSMA binding protein according to [3], wherein additionally amino acids corresponding to positions 6, 8, 9, 10, 12, and 46 of ubiquitin (SEQ ID NO: 1) are substituted or wherein additionally up to 6 amino acids are inserted between amino acids corresponding to positions 9 and 10 of ubiquitin (SEQ ID NO: 1) or wherein additionally amino acids corresponding to positions 11, 33, 51, 48, and 74 of ubiquitin (SEQ ID NO: 1) are substituted.

[7] The PSMA binding protein according to any one of [1]-[6] wherein the PSMA binding protein is a multimer comprising of a plurality of the PSMA binding protein according to any one of [1]-[6], preferably a dimer of the PSMA binding protein according to any one of [1]-[6].

[8] The PSMA binding protein according to any one of [1]-[7], comprising or consisting of an amino acid sequence selected from the group of SEQ ID NOs: 3-55, or selected from amino acid sequences with at least 90% identity thereto, respectively.

[9] The PSMA binding protein according to any one of [1]-[8], wherein the PSMA binding protein has a specific binding affinity to the extracellular domain of PSMA of 500 nM or less.

[10] The PSMA binding protein according to any one of [1]-[9], further comprising one or more coupling sites for the coupling of chemical moieties, preferably wherein the chemical moieties are selected from any of chelators, drugs, toxins, dyes, and small molecules.

[11] The PSMA binding protein according to any one of [1]-[10], further comprising at least one diagnostically active moiety, optionally selected from a radionuclide, fluorescent protein, photosensitizer, dye, or enzyme, or any combination of the above.

[12] The PSMA binding protein according to any one of [1]-[11], further comprising at least one therapeutically active moiety, optionally selected from a monoclonal antibody or a fragment thereof, a binding protein, a radionuclide, a cytotoxic compound, a cytokine, a chemokine, an enzyme, or derivatives thereof, or any combination of the above.

[13] The PSMA binding protein according to any one of [1]-[12], further comprising at least one moiety modulating pharmacokinetics optionally selected from a polyethylene glycol, a human serum albumin, an albumin-binding protein, an immunoglobulin binding protein, or an immunoglobulin or immunoglobulin fragment, a polysaccharide, or an unstructured amino acid sequence comprising amino acids alanine, glycine, serine, proline.

[14] The PSMA binding protein according to any one of [1]-[13], for use in diagnosis or treatment of PSMA related tumors, preferably for imaging tumors and radiotherapy treatment of PSMA related tumors.

[15] A composition comprising the PSMA binding protein according to any one of [1]-[14] for use in medicine, preferably for use in the diagnosis or treatment of PSMA related tumors, preferably for imaging tumors and radiotherapy treatment of PSMA related tumors.

[16] A method of producing the PSMA binding protein according to any one of [1]-[15], comprising the steps of a) culturing a host cell under conditions suitable to obtain said PSMA binding protein and b) isolating said PSMA binding protein produced.

This summary does not necessarily describe all features of the present invention. Other embodiments come apparent from a review of the ensuing detailed description.

BRIEF DESCRIPTION OF THE FIGURES

The Figures show:

FIG. 1-3 show examples for PSMA binding proteins with characteristic motifs in amino acids corresponding to positions 62-66 of SEQ ID NO: 1 (ubiquitin). Structural characteristics of such ubiquitin muteins are shown by the corresponding amino acids that are substituted in ubiquitin (numbers in the top row) or inserted between position 9 and 10 of ubiquitin (numbers in the top row: 9a, 9b, 9c, 9d, 9e, 9f in FIG. 2). Functional characteristics are shown as affinity to PSMA as determined by SPR (Biacore), thermal stability as determined by DSF, and cellular binding as described in Examples.

FIG. 1 shows PSMA binding proteins with 5-amino acid motif WWNPN (SEQ ID NO: 61) in positions 62-66. Amino acids corresponding to positions 6-, 8-, 9-, 10, 12, 42, 44, 46, 62-66, 68, 70, 72 of ubiquitin are substituted. In some binding proteins, further substitutions are found, as indicated in the column further substitution.

FIG. 2 shows PSMA binding proteins with 5-amino acid motif KHNTW (SEQ ID NO: 59) corresponding to positions 62-66. Amino acids corresponding to positions 42, 44, 62-66, 68, 70, 72 of ubiquitin are substituted, and 6 amino acids are inserted between position 9 and 10 of ubiquitin. In some binding proteins, further substitutions are found, as indicated in the column "further substitution".

FIG. 3 shows PSMA binding proteins with 5-amino acid motif GFAHR (SEQ ID NO: 56) or GWAHR (SEQ ID NO: 57) (or similar) and/or 5-amino acid WTTTF (SEQ ID NO: 58), WTPSI (SEQ ID NO: 75), WTPTI (SEQ ID NO: 80), or GDGDV (SEQ ID NO: 77). Amino acids corresponding to positions 6-, 8-, 62-66 of ubiquitin are substituted; two ubiquitin muteins are linked. In some PSMA binding proteins, further substitutions are found for example in positions 11, 33, 48, 51, 74 of ubiquitin, as indicated in the column "further substitution".

FIG. 4. Functional characterization of PSMA binding proteins as determined by flow cytometry. The histograms confirm binding of SEQ ID NO: 4 (referred to as 191871) on PSMA-overexpressing HEK293-cells or PSMA-expressing LNCaP-cells (grey peak); no binding on control cell lines HEK293-pEntry or PC3. Unmodified ubiquitin (bis-ubi; white peak) shows no binding on cells.

DETAILED DESCRIPTION OF THE INVENTION

The present inventors have developed a solution to meet the strong ongoing need in the art for expanding medical options for the diagnosis and treatment of cancer by providing novel PSMA binding proteins. The PSMA specific proteins as defined herein are functionally characterized by high specific affinity for PSMA. In particular, the invention provides PSMA binding proteins based on ubiquitin muteins (also known as Affilin® molecules). The PSMA binding proteins as described herein provide molecular formats with favorable physicochemical properties, high-level expression in bacteria, and allow easy production methods. The novel PSMA binding proteins may broaden so far unmet medical strategies for the diagnosis and therapy of PSMA related cancer. In particular, the PSMA binding proteins may be used for diagnostic or imaging purposes, for example, for the presence of tumor cells expressing PSMA, and for radiotherapy treatment of tumors expressing PSMA.

Before the present invention is described in more detail below, it is to be understood that this invention is not limited to the particular methodology, protocols and reagents described herein as these may vary. It is also to be understood that the terminology used herein is for the purpose of describing particular aspects and embodiments only and is not intended to limit the scope of the present invention which is reflected by the appended claims. Unless defined otherwise, all technical and scientific terms used herein have the same meaning as commonly understood by one of ordinary skill in the art to which this invention belongs. This includes a skilled person working in the field of protein engineering and purification, but also including a skilled person working in the field of developing new target-specific binding molecules for use in technical applications and in therapy and diagnostics.

Preferably, the terms used herein are defined as described in A multilingual glossary of biotechnological terms: (IUPAC Recommendations)", Leuenberger, H. G. W, Nagel, B. and Kölbl, H. eds. (1995), Helvetica Chimica Acta, CH-4010 Basel, Switzerland).

Throughout this specification and the claims, which follow, unless the context requires otherwise, the word "comprise", and variants such as "comprises" and "comprising", was understood to imply the inclusion of a stated integer or step, or group of integers or steps, but not the exclusion of any other integer or step or group of integers or steps. The term "comprise(s)" or "comprising" may encompass a limitation to "consists" or "consisting of", should such a limitation be necessary for any reason and to any extent.

Several documents (for example: patents, patent applications, scientific publications, manufacturer's specifications, instructions, GenBank Accession Number sequence submissions etc.) may be cited throughout the present specification. Nothing herein is to be construed as an admission that the invention is not entitled to antedate such disclosure by virtue of prior invention. Some of the documents cited herein may be characterized as being "incorporated by reference". In the event of a conflict between the definitions or teachings of such incorporated references and definitions or teachings recited in the present specification, the text of the present specification takes precedence.

All sequences referred to herein are disclosed in the attached sequence listing that, with its whole content and disclosure, forms part of the disclosure content of the present specification.

General Definitions

The term "PSMA" refers to a prostate specific membrane antigen. Human PSMA is a glycoprotein of about 100 kD with a short intracellular domain (residues 1-19), a transmembrane domain (residues 20-43), and an extracellular domain (residues 44-750). PSMA is represented by the UniProt ID Q04609 (version of Mar. 15, 2017); human PSMA mRNA is represented by the NCBI reference sequence NM_004476.1. The term PSMA comprises polypeptides which show a sequence identity of at least 70%, 80%, 85%, 90%, 95%, or 100% to Q04609.

The term "PSMA binding protein" refers to a protein with high affinity binding to PSMA.

The terms "protein" and "polypeptide" refer to any chain of two or more amino acids linked by peptide bonds, and does not refer to a specific length of the product. Thus, peptides, protein, amino acid chain, or any other term used to refer to a chain of two or more amino acids, are included within the definition of polypeptide", and the term polypeptide may be used instead of, or interchangeably with, any of these terms. The term polypeptide is also intended to refer to the products of post-translational modifications of the polypeptide, which are well known in the art.

The term "modification" or "amino acid modification" refers to a substitution, a deletion, or an insertion of an reference amino acid at a particular position in a parent polypeptide sequence by another amino acid. Given the known genetic code, and recombinant and synthetic DNA techniques, the skilled scientist can readily construct DNAs encoding the amino acid variants.

The term "mutein" as used herein refers to derivatives of, for example, ubiquitin according to SEQ ID NO: 1 or bis-ubiquitin according to SEQ ID NO: 2, or similar proteins, which differ from said amino acid sequence by amino acid exchanges, insertions, deletions or any combination thereof, provided that the mutein has a specific binding affinity to PSMA.

The term "Affilin®" (registered trademark of Navigo Proteins GmbH) refers to non-immunoglobulin derived binding proteins.

The term "substitution" is understood as exchange of an amino acid by another amino acid. The term "insertion" comprises the addition of amino acids to the original amino acid sequence.

The term ubiquitin refers to ubiquitin in accordance with SEQ ID NO: 1 or to bis-ubiquitin of SEQ ID NO: 2 and to proteins with at least 95% identity, such as for example with point mutations in positions 45, 75, 76 which do not influence binding to a target (PSMA).

The terms binding "affinity" and "binding activity" may be used herein interchangeably, and they refer to the ability of a polypeptide to bind to another protein, peptide, or fragment or domain thereof. Binding affinity is typically measured and reported by the equilibrium dissociation constant ($K_D$), which is used to evaluate and rank order strengths of bimolecular interactions.

The term fusion protein" relates to a protein comprising at least a first protein joined genetically to at least a second protein. A fusion protein is created through joining of two or more genes that originally coded for separate proteins. Fusion proteins may further comprise additional domains that are not involved in binding of the target, such as but not limited to, for example, multimerization moieties, polypeptide tags, polypeptide linkers or moieties binding to a target different from PSMA.

The term "amino acid sequence identity" refers to a quantitative comparison of the identity (or differences) of the amino acid sequences of two or more proteins. Percent (%) amino acid sequence identity" with respect to a reference polypeptide sequence is defined as the percentage of amino acid residues in a sequence that are identical with the amino acid residues in the reference polypeptide sequence, after aligning the sequences and introducing gaps, if necessary, to achieve the maximum percent sequence identity. To determine the sequence identity, the sequence of a query protein is aligned to the sequence of a reference protein or polypeptide. Methods for sequence alignment are well known in the art. For example, for determining the extent of an amino acid sequence identity of an arbitrary polypeptide relative to the amino acid sequence of the SIM Local similarity program as known in the art is preferably employed. For multiple alignment analysis, Clustal Omega is preferably used, as known to someone skilled in the art.

The term "multimeric binding molecules" refers to binding proteins comprising at least two, three, four, five or more binding proteins. Said binding proteins may bind specifically to the same or overlapping epitopes on a target antigen, for example overlapping epitopes of PSMA, or they may bind to different epitopes on a target antigen, for example different epitopes of PSMA.

The term "conjugate" as used herein relates to a protein comprising of at least a first protein, for example the PSMA binding protein of the invention, attached chemically to other substances such as to a non-proteinaceous (chemical) moiety or to a second protein.

The term "epitope" includes any molecular determinant capable of being bound by a binding protein as defined herein and is a region of a target antigen (i.e. PSMA) that is bound by a binding protein, and may include specific amino acids that directly contact the binding protein.

DETAILED DESCRIPTION OF THE EMBODIMENTS OF THIS INVENTION

Structural Characterization of PSMA Binding Proteins.

The prostate specific membrane antigen (PSMA) binding protein as defined herein comprises at least one amino acid binding motif selected from the group consisting of GFAHR (SEQ ID NO: 56), GWAHR (SEQ ID NO: 57), SFAHR (SEQ ID NO: 72), SYAHR (SEQ ID NO: 73), GFAHL (SEQ ID NO: 74), WTTTF (SEQ ID NO: 58), WTPSI (SEQ ID NO: 75), WTETI (SEQ ID NO: 76), GDGDV (SEQ ID NO: 77) KHNTW (SEQ ID NO: 59), VAYRP (SEQ ID NO: 60), and WWNPN (SEQ ID NO: 61), or amino acid motifs with at least 80% identity thereto, respectively. In various embodiments, the PSMA binding protein comprises a mutein of ubiquitin (SEQ ID NO: 1). In various embodiments, the PSMA binding protein comprises an amino acid binding motif selected from the group of GFAHR (SEQ ID NO: 56), GWAHR (SEQ ID NO: 57), SFAHR (SEQ ID NO: 72), SYAHR (SEQ ID NO: 73), GFAHL (SEQ ID NO: 74), WTTTF (SEQ ID NO: 58), WTPSI (SEQ ID NO: 75), WTETI (SEQ ID NO: 76), GDGDV (SEQ ID NO: 77), KHNTW (SEQ ID NO: 59), VAYRP (SEQ ID NO: 60), and WWNPN (SEQ ID NO: 61), or similar motifs, wherein the amino acid residues of the binding motif correspond to positions 62, 63, 64, 65, 66 of ubiquitin according to SEQ ID NO: 1. In various embodiments, the PSMA binding protein comprises a mutein of ubiquitin according to SEQ ID NO: 1 wherein the ubiquitin mutein comprises at least one amino acid binding motif selected from GFAHR (SEQ ID NO: 56). GWAHR (SEQ ID NO: 57), SFAHR (SEQ ID NO: 72), SYAHR (SEQ ID NO: 73), GFAHL (SEQ ID NO: 74), WTTTF (SEQ ID NO: 58), WTPSI (SEQ ID NO: 75), WTETI (SEQ ID NO: 76), GDGDV (SEQ ID NO: 77), KHNTW (SEQ ID NO: 59), VAYRP (SEQ ID NO: 60), and WWNPN (SEQ ID NO: 61), or similar motifs, in positions that correspond to positions 62, 63, 64, 65, 66 of ubiquitin (SEQ ID NO: 1).

PSMA Binding Proteins with Motif WWNPN

In various embodiments, PSMA binding proteins have a characteristic amino acid motif VWVNPN in positions 62, 63, 64, 65, 66 of ubiquitin (SEQ ID NO: 1). In various embodiments, the PSMA binding protein comprises a mutein of ubiquitin according to SEQ ID NO: 1 wherein the ubiquitin mutein comprises an amino acid binding motif WWNPN in positions that correspond to positions 62, 63, 64, 65, 66 of ubiquitin (SEQ ID NO: 1), and further substitutions in positions corresponding to position 6, 8, 9, 10, 12, 42, 44, 46, 68, 70, 72 of SEQ ID NO: 1. In some embodiments, PSMA binding proteins comprise or consist of at least one ubiquitin mutein modified by, in addition to Q62W, K63W, E64N, S65P, and T66N, further substitutions selected from the group of K6Y or K6W; L8R or L8A or L8K; T9A, T9V, T9E, or T9Q; G10L or G10F; T12Q; R42M or R42K or R42T; I44F or I44K; A46K or A46R; H68S; V70N or V70D; R72D or R72N or R72G. In some embodiments, PSMA binding proteins comprise ubiquitin muteins with additional 1, 2, or 3 substitutions, for example but not limited to selected from the group of E16A, E18G, I23V, K29R, Q31R, K33R, I36T, K48R, L71R, and L73R (for example, see SEQ ID NOs: 38, 39, 40, 41, 47, 48, 49, 50, 51).

In various embodiments, the PSMA binding protein comprises or consists of an ubiquitin mutein with substitutions in amino acid positions 6-, 8-, 9-, 10, 12, 42, 44, 46, 62, 63, 64, 65, 66, 68, 70, and 72 of SEQ ID NO: 1 wherein the ubiquitin mutein has a characteristic five amino acid motif WWNPN (SEQ ID NO: 61) in positions 62, 63, 64, 65, 66. FIG. 1 shows examples for PSMA binding proteins with amino acid substitutions in positions 6, 8, 9, 10, 12, 42, 44, 46, 62, 63, 64, 65, 66, 68, 70, and 72 of SEQ ID NO: 1.

In one embodiment, the PSMA binding protein comprises one or more amino acids selected from the group consisting of SEQ ID NOs: 35-51, for example but not limited to SEQ ID NO: 40 (Affilin-187191) (differences to SEQ ID NO: 1 that result in PSMA binding are underlined). MQIFV<u>Y-TRALKQ</u>ITLEVEPSDTIENVKAKIQDKEG-IPPDQQ<u>M</u>LFWK<u>G</u>RQLEDGRTLSDY NIW<u>WNPN</u>LSL<u>N</u>L<u>D</u>LRAA (SEQ ID NO: 40).

PSMA Binding Proteins with Motif KHNTW or VAYRP

In various embodiments, PSMA binding proteins have a characteristic amino acid motif KHNTW in positions 62, 63, 64, 65, 66 of ubiquitin (SEQ ID NO: 1). In various embodiments, the PSMA binding proteins comprises or consists of an ubiquitin mutein modified by substitutions selected from R42H, I44Y, Q62K, K63H, E64N, S65T, T66W, H68E, V70M, and R72F of ubiquitin (SEQ ID NO: 1).

In various embodiments, the PSMA binding protein has a characteristic amino acid motif VAYRP in positions 62, 63, 64, 65, 66 of ubiquitin (SEQ ID NO: 1). In other embodiments, the PSMA binding proteins comprises or consists of an ubiquitin mutein modified by substitutions selected from R42I, I44W, Q62V, K63A, E64Y, S65R, T66P, H68Y, V70T, and R72A of ubiquitin (SEQ ID NO: 1).

In some embodiments, the PSMA binding protein comprises a ubiquitin mutein that is additionally modified by an insertion of 4-8 amino acids between amino acids T9 and G10 of ubiquitin (SEQ ID NO: 1), preferably by an insertion of 6 amino acids. In various embodiments, the PSMA binding protein has an insertion of an 6 amino acid motif between position 9 and 10, wherein the amino acid in the 6th position is preferably an aromatic amino acid, or M. Amino acid motifs of such insertion may include but are not limited to: FEHXSF (SEQ ID NO: 81), wherein X is selected from any amino acid, preferably P, H, K, or N; PQPPEX (SEQ ID NO: 82), wherein X is selected from W, F, or Y; PPFAFW (SEQ ID NO: 83), PIPPDW (SEQ ID NO: 84), or DMYRFM (SEQ ID NO: 85).

In various embodiments, the PSMA binding protein comprises or consists of a mutein of ubiquitin according to SEQ ID NO: 1 wherein the ubiquitin mutein comprises at least one amino acid binding motif selected from KHNTW (SEQ ID NO: 59) or VAYRP (SEQ ID NO: 60) in positions that correspond to positions 62, 63, 64, 65, 66 of ubiquitin (SEQ ID NO: 1), and further substitutions in positions corresponding to position 42, 44, 68, 70, 72 of ubiquitin (SEQ ID NO: 1), and an insertion of 4-8 amino acids between amino acids T9 and G10 of ubiquitin (SEQ ID NO: 1). In various embodiments, the PSMA binding protein comprises or consists of an ubiquitin mutein with substitutions in amino acids corresponding to positions 42, 44, 62, 63, 64, 65, 66, 68, 70, and 72 of SEQ ID NO: 1 and an insertion of 6 amino acids at position 9 of SEQ ID NO: 1 and wherein the ubiquitin muteins have a characteristic five amino acid motif KHNTW (SEQ ID NO: 59) or VAYRP (SEQ ID NO: 60) corresponding to positions 62, 63, 64, 65, 66. Additional 1, 2, or 3 positions might be substituted, for example, but not limited to, A46V of ubiquitin (see SEQ ID NO: 29).

FIG. 2 shows examples for specific amino acids in positions 42, 44, 62, 63, 64, 65, 66 of SEQ ID NO: 1 and an insertion of 6 amino acids between position 9 and 10 (shown as 9a, 9b, 9c, 9d, 9e, 9f in FIG. 2) of SEQ ID NO: 1.

In one embodiment, the PSMA binding comprises amino acids selected from the group consisting of SEQ ID NOS: 25-34, for example SEQ ID NO: 25 (Affilin-164667) MQIFV<u>K</u>TLT<u>FEHP</u>SFGKTITLEVEPSDTIENVKAKIQD-KEGIPPDQQ<u>HLY</u>WAGK QLEDGR TLS-DYNI<u>KHNTW</u>LEL<u>M</u>LFLRAA (SEQ ID NO: 25; differences to SEQ ID NO: 1 that result in PSMA binding are underlined).

PSMA Binding Proteins with Motif GWAHR (SEQ ID NO: 57)/GFAHR (SEQ ID NO: 56) or Similar and or WTTTF (SEQ ID NO: 58) or Similar In some embodiments, the PSMA binding protein comprises a ubiquitin mutein with characteristic five amino acid motif GWAHR (SEQ ID NO: 57) or GFAHR (SEQ ID NO: 56) or SFAHR (SEQ ID NO: 72) or SYAHR (SEQ ID NO: 73) or GFAHL (SEQ ID NO: 74) or variants thereof in positions 62, 63, 64, 65, 66 of ubiquitin. In some embodiments, the PSMA binding protein comprises one or more ubiquitin mutein(s) based on ubiquitin according to SEQ ID NO: 1 and comprising an amino acid binding motif GFAHR (SEQ ID NO: 56), or a motif with 80% identity thereto, at amino acid residues that correspond to positions 62, 63, 64, 65, 66 of ubiquitin according to SEQ ID NO: 1. In some embodiments, the PSMA binding protein comprises one or more ubiquitin mutein(s) based on ubiquitin according to SEQ ID NO: 1 and comprising an amino acid binding motif $X_1X_2AHX_3$, wherein $X_1$ is selected from G or S, $X_2$ is selected from an aromatic amino acid, preferably W or F, $X_3$ is selected from R or L, at amino acid residues that correspond to positions 62, 63, 64, 65, 66 of ubiquitin according to SEQ ID NO: 1. In some embodiments, the PSMA binding protein comprises one or more ubiquitin mutein(s) based on ubiquitin according to SEQ ID NO: 1 and comprising an amino acid binding motif G(X)AHR (SEQ ID NO: 86), wherein X is an aromatic amino acid residue, preferably wherein X is selected from F or W. In some embodiments, the PSMA binding protein comprises one or more ubiquitin mutein(s) based on ubiquitin according to SEQ ID NO: 1 and comprising an amino acid binding motif GFAHR (SEQ ID NO: 56), GWAHR (SEQ ID NO: 57), SFAHR (SEQ ID NO: 72), or SYAHR (SEQ ID NO: 73) or GFAHL (SEQ ID NO: 74), at amino acid residues that correspond to positions 62, 63, 64, 65, 66 of ubiquitin according to SEQ ID NO: 1.

In other embodiments, the PSMA binding protein comprises a ubiquitin mutein with characteristic five amino acid motif WTTTF (SEQ ID NO: 58) or WTPSI (SEQ ID NO: 75) or WTETI (SEQ ID NO: 76) or GDGDV (SEQ ID NO: 77) or variants thereof in positions 62, 63, 64, 65, 66 of ubiquitin. In some embodiments, the PSMA binding protein comprises or consists of two ubiquitin moieties where the first ubiquitin moiety has the motif GFAHR (SEQ ID NO: 56) or GWAHR (SEQ ID NO: 57) or SFAHR (SEQ ID NO: 72) or SYAHR (SEQ ID NO: 73) or GFAHL (SEQ ID NO: 74) or similar motif or the second ubiquitin moiety has the motif WTTTF (SEQ ID NO: 58) or WTPSI (SEQ ID NO: 75) or WTETI (SEQ ID NO: 76) or GDGDV (SEQ ID NO: 77) or similar motifs. In various embodiments, the PSMA binding protein comprises or consists of two ubiquitin moieties where the first ubiquitin moiety has the motif GFAHR (SEQ ID NO: 56) or GWAHR (SEQ ID NO: 57) or SFAHR (SEQ ID NO: 72) or SYAHR (SEQ ID NO: 73) or GFAHL (SEQ ID NO: 74), or similar motif, and the second ubiquitin moiety has the motif WTTTF (SEQ ID NO: 58) or WTPSI (SEQ ID NO: 75) or WTETI (SEQ ID NO: 76) or GDGDV (SEQ ID NO: 77), or similar motif. FIG. 3 shows examples for specific amino acids in positions 6, 8, 62, 63, 64, 65, 66 in PSMA binding proteins consisting of two ubiquitin moieties. In various embodiments, the PSMA binding protein comprises or consists of two ubiquitin muteins with substitutions in amino acids corresponding to positions 6, 8, 62, 63, 64, 65, 66 of SEQ ID NO: 1 fused to each other, wherein the N-terminal located ubiquitin mutein has a characteristic five amino acid motif GFAHR (SEQ ID NO: 56) or GWAHR (SEQ ID NO: 57) or SFAHR (SEQ ID NO: 72) or SYAHR SEQ ID NO: 73) or GFAHL (SEQ ID NO: 74) corresponding to positions 62, 63, 64, 65, 66, and the C-terminal located ubiquitin mutein has a characteristic five amino acid motif WTTTF (SEQ ID NO: 58) or WTPSI (SEQ ID NO: 75) or WTETI (SEQ ID NO: 76) or GDGDV (SEQ ID NO: 77) corresponding to positions 62, 63, 64, 65, 66, as shown in FIG. 3.

In some embodiments, ubiquitin mutein has substitutions selected from K6R or K6W; L8M, L8P, L8Q, L8W, L8D, L8G, L8H, or L8I; Q62G, Q62S, or Q62W; K63F, K63W, K63G, K63P, or K63Y; E64A or E64G; S65H or S65D; and T66R, T66Q, or T66L. In some embodiments, the ubiquitin mutein has substitutions selected from K6M, K6L, K6A, or K6H; L8Q, L8R, L8F, L8N, or L8H; Q62W or Q62G; K63T, K63H, or K63D; E64T, E64P, E64E, or E64G; S65T, S65Y, or S65D, and T66F, T66I, T66L, or T66V.

In some embodiments, the PSMA binding protein comprises an ubiquitin mutein additionally modified by further substitutions, for example but not limited to positions 10, 11, 33, 48, 48, 51, 74 of ubiquitin, in specific embodiments for example selected from the group of G10Q, K11Q, K33T, K48T, E51A, R74C of ubiquitin (for example, see SEQ ID NOs: 11, 12, 17, 19).

In some embodiments, PSMA binding proteins comprise of two ubiquitin muteins linked to each other, i.e. PSMA binding proteins comprise of muteins of bis-ubiquitin (SEQ ID NO: 2).

In one embodiment, the PSMA binding protein comprises one or more amino acids selected from the group consisting of SEQ ID NOs: 3-24, for example (differences to SEQ ID NO: 1 or SEQ ID NO: 2 that result in PSMA binding are underlined).

```
(Affilin-162462)
                                   SEQ ID NO: 3
MQIFVRTPTGKTITLEVEPSDTIENVKAKIQDKEGIPPDQQRLIWAGKQL

EDGRTLSDYNIGFAHRLHLVLRLRAAMQIFVMTQTGKTITLEVEPSDTIE

NVKAKIQDKEGIPPDQQRLIWAGKQLEDGRTLSDYNIWTTTFLHLVLRL

RAA;

(Affilin-191871)
                                   SEQ ID NO: 4
MQIFVRTQTGKTITLEVEPSDTIENVKAKIQDKEGIPPDQQRLIWAGKQL

EDGRTLSDYNIGWAHRLHLVLRLRAAMQIFVHTNTGKTITLEVEPSDTIE

NVKAKIQDKEGIPPDQQRLIWAGKQLEDGRTLSDYNIWTETILHLVLRL

RAA.
```

The PSMA binding protein of the invention comprises or consists of an amino acid sequence selected from the group consisting of SEQ ID NOs: 3-55. In some embodiments, the PSMA binding protein comprises an amino acid sequence that exhibits at least 90%, at least 91%, at least 92%, at least 93%, at least 94%, at least 95%, at least 96%, at least 97%, at least 98%, at least 99%, or 100% sequence identity to one or more of the amino acid sequences of SEQ ID NOs: 3-55. For example, but not limited to, amino acid sequences of selected PSMA binding proteins are shown in FIG. 1, FIG. 2, and FIG. 3.

In some embodiments, the PSMA binding protein as disclosed herein has at least 74%, 75%, 76%, 77%, 78%, or 79% sequence identity to the amino acid sequence of SEQ ID NO: 1 or SEQ ID NO: 2. In various embodiments, the PSMA binding protein as disclosed herein has at least 80% sequence identity to the amino sequence of SEQ ID NO: 1 or SEQ ID NO: 2. The PSMA binding protein as disclosed herein has at least 81%, 82%, 83%, 84%, or 85% sequence identity to the amino acid sequence of SEQ ID NO: 1 or SEQ ID NO: 2. In some embodiments, the PSMA binding protein as disclosed herein may have any amino acid identity between 74% identity and 90% identity to the amino acid sequence of ubiquitin (SEQ ID NO: 1) or bis-ubiquitin (SEQ ID NO: 2).

In some embodiments, the PSMA binding protein as disclosed herein may have any amino acid identity of at least 90% to the amino acid sequence of SEQ ID NO: 3. In some embodiments, the PSMA binding protein as disclosed herein may have any amino acid identity of at least 90% to the amino acid sequence of SEQ ID NO: 4. In some embodiments, the PSMA binding protein as disclosed herein may have any amino acid identity of at least 90% to the amino acid sequence of SEQ ID NO: 25. In some embodiments, the PSMA binding protein as disclosed herein may have any amino acid identity of at least 90% to the amino acid sequence of SEQ ID NO: 26. In some embodiments, the PSMA binding protein as disclosed herein may have any amino acid identity of at least 90% to the amino acid sequence of SEQ ID NO: 40.

Multimers.

In preferred embodiments, the PSMA binding protein is a multimer comprising of a plurality of the PSMA binding protein as defined herein. A multimer may comprise two, three, four, or more PSMA binding proteins. In one embodiment, the PSMA binding protein comprises 2, 3, 4, or more PSMA binding proteins linked to each other, i.e. the PSMA-binding protein can be a dimer, trimer, or tetramer, etc. In some embodiments, the multimer is a dimer of the PSMA binding protein as defined above. In various embodiments, the PSMA binding protein is a homodimer. A homodimeric PSMA binding protein as understood herein is a protein wherein two PSMA binding proteins with identical amino acid sequences are linked to each other. Homo-dimers can be generated by fusing two identical proteins of any one of the group of SEQ ID NO: 3-51 or of any of the amino acid sequences with at least 90% identity thereto. For example, but not limited to, homodimers are exemplied in SEQ ID NO: 52 (dimer of SEQ ID NO: 3) and SEQ ID NO: 53 (dimer of SEQ ID NO: 25).

In other embodiments the multimer is a heterodimer, e.g. the two amino acid sequences of the PSMA binding proteins are different. For example, heterodimers were generated, as shown in SEQ ID NO: 54 (dimer of SEQ ID NO: 25 and SEQ ID NO: 3, from N- to C-terminus) and SEQ ID NO: 55 (dimer of SEQ ID NO: 3 and SEQ ID NO: 25, from N- to C-terminus).

In some embodiments, two or more PSMA binding proteins are directly linked. In some embodiments, two or more PSMA binding proteins are linked by a peptide linker. In various embodiments, two or more PSMA binding proteins are linked via a peptide linker of up to 30 amino acids. In other embodiments, two or more PSMA binding proteins are linked via a peptide linker of 10, 11, 12, 13, 14, 15, 16, 17, 18, 19, 20 amino acids. In one embodiment, two PSMA binding proteins are linked by 16 amino acids.

One embodiment relates to a linker that is comprised of amino acids selected from at least two or more of the group of glycine, serine, alanine, or proline. In some embodiments two or more PSMA binding proteins are linked via a peptide linker of the amino acid sequence according to any one of SAPAASPSPAAPAPSPASPAPASPASAPSAPASAP-PAASA (SEQ ID NO: 62) or PAAPAPSPASPAPASPASAPS (SEQ ID NO: 63) or peptide linkers with at least 90% identity thereto. Other linkers for the fusion of proteins are known in the art and can be used.

Functional Characterization.

In some embodiments, the PSMA binding protein as described herein binds to PSMA expressed on cells as determined by FACS and/or has a binding affinity to PSMA of 500 nM or less as determined by surface plasmon resonance assays.

In some embodiments, the PSMA binding protein as described herein has a binding affinity (KD) of less than 500 nM for PSMA. The PSMA binding proteins bind PSMA with measurable binding affinity of less than 500 nM, less than 200 nM, less than 100 nM, less than 50 nM, less than 20 nM, less than 10 nM, less than 5 nM, and less than 1 nM. The appropriate methods are known to those skilled in the art or described in the literature. The methods for determining the binding affinities are known perse and can be selected for instance from the following methods known in the art: enzyme-linked immunosorbent assay (ELISA), surface plasmon resonance (SPR), kinetic exclusion analysis (KinExA assay), Bio-layer interferometry (BLI), flow cytometry, fluorescence spectroscopy techniques, isothermal titration calorimetry (ITC), analytical ultracentrifugation, radioimmunoassay (RIA or IRMA), and enhanced chemiluminescence (ECL). Some of the methods are described in the Examples below. Typically, the dissociation constant $K_D$ is determined at the range of temperatures between 20° C. and 30° C., for example at 20° C., 25° C., or 30° C. If not specifically indicated otherwise, the $K_D$ values recited herein are determined at 25° C. by SPR. The lower the $K_D$ value, the greater the binding affinity of the biomolecule for its binding partner. The higher the $K_D$ value, the weaker the binding partners bind to each other. Examples are provided in FIG. 1, FIG. 2, FIG. 3 and in the Examples. The binding of the PSMA binding protein as described herein is highly specific for PSMA. Ubiquitin (SEQ ID NO: 1) does not bind to PSMA. The PSMA binding protein as described herein binds to PSMA but does not detectably bind to human Fc-domain of immunoglobulin IgG$_1$, as determined by surface plasmon resonance assays. A binding to PSMA with $K_D$ less than 500 nM may be important for targeted medical applications for PSMA related cancer. Further, a protein with PSMA binding with $K_D$ less than 500 nM may have reduced potential toxic side effects. In some embodiments, the PSMA binding protein comprises a ubiquitin mutein that has (a) a five amino acid residue motif at positions corresponding to positions 62, 63, 64, 65, and 66 of ubiquitin (SEQ ID NO: 1) selected from the group of GFAHR (SEQ ID NO: 56), GWAHR (SEQ ID NO: 57), SFAHR (SEQ ID NO: 72), SYAHR (SEQ ID NO: 73), GFAHL (SEQ ID NO: 74), WTTTF (SEQ ID NO: 58), WTPSI (SEQ ID NO: 75), WTETI (SEQ ID NO: 76), GHEYL (SEQ ID NO: 79), GDGDV (SEQ ID NO: 77) KHNTW (SEQ ID NO: 59), VAYRP (SEQ ID NO: 60), and WWNPN (SEQ ID NO: 61), or motifs with 80% identity thereto; (b) 80% to 93% sequence identity to SEQ ID NO: 1; and (b) a binding affinity ($K_D$) of less than 500 nM for PSMA. The half maximal effective concentration $EC_{50}$ refers to the concentration of a PSMA binding protein which induces a response halfway between the baseline and maximum after a specified exposure time and thus represents the concentration of a PSMA binding protein where 50% of its maximal effect is observed, in this case half-maximal fluorescence intensity signal in a cell binding, flow cytometry experiment. In some embodiments, the PSMA binding protein as described herein has an $EC_{50}$ of less than 100 nM for PSMA-expressing cells, less than 50 nM, less than 20 nM, less than 10 nM, less than 5 nM, and less than 1 nM. In some embodiments, the PSMA binding protein as described herein has an $EC_{50}$ to PSMA-expressing cells of less than 1 nM after incubation in the presence of mouse serum for at least 24 h at 37° C. The appropriate methods are known to those skilled in the art. The lower the $EC_{50}$ value, the greater the binding of the PSMA binding protein for PSMA. Examples for PSMA binding proteins that are stable even in the presence of serum are provided in Table 4.

In some embodiments, the PSMA binding protein as described herein is stable at high temperatures, up to 85° C. For stability analysis, for example spectroscopic or fluorescence-based methods in connection with chemical or physical unfolding are known to those skilled in the art. For example, the stability of a molecule can be determined by measuring the thermal melting ($T_m$) temperature, the temperature in ° Celsius (° C.) at which half of the molecules become unfolded, using standard methods. Typically, the higher the $T_m$, the more stable the molecule. Temperature stability was determined by differential scanning fluorimetry (DSF), as described in further detail in Examples and in FIG. 1, FIG. 2, FIG. 3.

Competitive binding experiments comparing PSMA binding proteins show that PSMA binding proteins with different motifs may bind non identical or non-overlapping epitopes (see Examples). For example, SEQ ID NO: 25 with motif KHNTW (SEQ ID NO: 59) binds to a different epitope than SEQ ID NO: 15 with motifs GFAHR (SEQ ID NO: 56) and WTTTF (SEQ ID NO: 58). Thus, certain PSMA binding proteins do not compete for PSMA binding, and are particularly suitable for certain diagnostic or therapeutic applications. Additional functional characterization was performed by cellular PSMA binding analysis with PSMA overexpressing cells. Immunofluorescence microscopy and flow cytometric analysis confirmed the specific binding of PSMA binding proteins as described herein to PSMA-positive tumor cell lines from human origin and to PSMA on live cells (see Examples).

Coupling Sites.

In some embodiments, the PSMA binding protein as described herein further comprises one or more coupling site(s) for the coupling of chemical moieties. A coupling site is capable of reacting with other chemical groups to couple the PSMA binding protein to chemical moieties. The defined number and defined position of coupling sites enables site-specific coupling of chemical moieties to the PSMA binding proteins as described herein. Thus, a large number of chemical moieties can be bound to a PSMA binding protein if required. The number of coupling sites can be adjusted to the optimal number for a certain application by a person skilled in the art to adjust the amount of the chemical moieties accordingly. In selected embodiments, the coupling site may be selected from the group of one or more amino acids which can be labeled with specific chemistry such as one or more cysteine residues, one or more lysine residues, one or more tyrosine residues, one or more tryptophan residues, or one or more histidine residues. The PSMA binding protein may comprise 1 to 20 coupling site(s), such as 1 to 6 coupling site(s), such as 2 coupling sites, or one coupling site.

Coupling Domains.

One embodiment provides a PSMA binding protein that comprises at least one coupling domain of 1 to 80 amino acids comprising one or more coupling sites. In some embodiments, the coupling domain of 1 to 80 amino acids may comprise alanine, proline, or serine, and as coupling site cysteine. An example for a PSMA binding protein with a coupling domain of amino acids SAC is provided in SEQ ID NO: 5 (Affilin-191871 with c-terminal amino acids SAC). In other embodiments, the coupling domain of 1 to 80 amino acid residues may consist of alanine, proline, serine, and as coupling site cysteine. In one embodiment, the coupling domain is consisting of 20-60% alanine, 20-40% proline, 10-60% serine, and one or more cysteine residues as coupling site(s) at the C- or N-terminal end of the PSMA binding protein as described herein. In some embodiments the amino acids alanine, proline, and serine are randomly distributed throughout a coupling domain amino acid sequence so that not more than a maximum of 2, 3, 4, or 5 identical amino acid residues are adjacent, preferably a maximum of 3 amino acids. The composition of the 1 to 20 coupling domains can be different or identical.

Amino acid compositions of selected examples for coupling domains with coupling site (Cysteine) are shown in Table 1.

TABLE 1

| Amino acid compositions of examples for coupling domains | |
|---|---|
| amino acid sequence | SEQ ID NO: |
| SAPAPSAPAASAPPAPAAPCAPAAPASAPAPAS APAASPCPAAPAPSPASPAPASPASAPS | 64 |
| SAPAPSAPAASAPPAPAAPCAPAAPASAPAPAS APAASPC | 65 |
| SAPAPSAPAASAPPAPAAPC | 66 |
| APAAPASAPAPASAPAASPC | 67 |
| SAPAPSAPAASAPPAPAAPAAPAAPASAPAPAC | 68 |
| APAASPSPAAPAPSPASPAPASPASAPSAPASC | 69 |

In some embodiments, the chemical moieties are selected from any of chelators, drugs, toxins, dyes, and small molecules. In some embodiments, at least one of the chemical moieties is a chelator designed as a complexing agent for coupling one or more further moieties to the targeted compound to the PSMA binding protein as disclosed herein. One embodiment relates to a PSMA binding protein wherein the chelator is a complexing agent for coupling one or more radioisotopes or other detectable labels, as described in the Examples.

Diagnostic Moiety.

In various embodiments, the PSMA binding protein further comprises a diagnostic moiety. In other embodiments, the PSMA binding protein further comprises more than one diagnostic moiety. In some embodiments, such diagnostic moiety may be selected from radionuclides, fluorescent proteins, photosensitizers, dyes, or enzymes, or any combination of the above. In some embodiments, a PSMA binding protein that comprises at least one diagnostic moiety can be employed, for example, as imaging agent, for example to evaluate presence of tumor cells or metastases, tumor distribution, and/or recurrence of tumor. Methods for detection or monitoring of cancer cells involve imaging methods. Such methods involve imaging PSMA related cancer cells by, for example, radioimaging or photoluminescens or fluorescence.

Therapeutic Moiety.

In various embodiments, the PSMA binding protein further comprises a therapeutically active moiety. In other embodiments, the PSMA binding protein further comprises more than one therapeutically active moiety. In some embodiments, such therapeutically active moiety may be selected from a monoclonal antibody or a fragment thereof, a binding protein such as an ubiquitin mutein (Affilin), an extracellular domain of a receptor or fragments thereof, a radionuclide, a cytotoxic compound, a cytokine, a chemokine, an enzyme, or derivatives thereof, or any combination of the above. In some embodiments, the PSMA binding protein that comprises a therapeutically active component may be used in targeted delivery of any of the above listed components to the PSMA expressing tumor cell and accumulate therein, thereby resulting in low levels of toxicity to normal cells.

Radionuclides.

Suitable radionuclides for applications in imaging in vivo or in vitro or for radiotherapy include for example but are not limited to the group of gamma-emitting isotopes, the group of positron emitters, the group of beta-emitters, and the group of alpha-emitters. In some embodiments, suitable conjugation partners include chelators such as 1,4,7,10-tetraazacyclododecane-1,4,7,10-tetraacetic acid (DOTA) or diethylene triamine pentaacetic acid (DTPA) or their activated derivatives, nanoparticles and liposomes. In various embodiments, DOTA may be suitable as complexing agent for radioisotopes and other agents for imaging, as described in the Examples in further detail.

Moiety Modulating Pharmacokinetics.

In some embodiments, the PSMA binding protein further comprises at least one moiety modulating pharmacokinetics optionally selected from a polyethylene glycol, a human serum albumin, an albumin-binding protein, an immunoglobulin binding protein or an immunoglobulin or immunoglobulin fragments, a polysaccharide (for example, hydroxylethyl starch), or an unstructured amino acid sequence which increases the hydrodynamic radius such as a multimer comprising amino acids alanine, glycine, serine, proline. In various embodiments, said moiety increases the half-life of the PSMA binding protein at least 1.5 fold. Several techniques for producing PSMA binding protein with extended half-life are known in the art, for example, direct fusions of the moiety modulating pharmacokinetics with the PSMA binding protein as described above or chemical coupling methods. The moiety modulating pharmacokinetics can be attached for example at one or several sites of the PSMA binding protein through a peptide linker sequence or through a coupling site as described above.

Conjugation of proteinaceous or non-proteinaceous moieties to the PSMA binding protein may be performed applying chemical methods well-known in the art. In some embodiments, coupling chemistry specific for derivatization of cysteine or lysine residues may be applicable. Chemical coupling can be performed by chemistry well known to someone skilled in the art, including but not limited to, substitution, addition or cycloaddition or oxidation chemistry (e.g. disulfide formation).

Molecules for Purification/Detection.

In some embodiments, additional amino acids can extend either at the N-terminal end of the PSMA binding protein or the C-terminal end or both. Additional sequences may include for example sequences introduced e.g. for purification or detection. In one embodiment, additional amino acid sequences include one or more peptide sequences that confer an affinity to certain chromatography column materials. Typical examples for such sequences include, without being limiting, Strep-tags (see e.g. SEQ ID NO: 71), oligohistidine-tags, glutathione S-transferase, maltose-binding protein, inteins, intein fragments, or the albumin-binding domain of protein G.

Use in Medicine.

Various embodiments relate to the PSMA binding protein as disclosed herein for use in medicine. In one embodiment, the PSMA binding protein is used in medicine to diagnose or treat cancer associated with PSMA expression. The PSMA binding proteins as disclosed herein allow selective diagnosis and treatment of PSMA related cancer cells or cancer tissues. PSMA is known to be upregulated in tumor cells. PSMA is highly expressed in prostate cancer and metastases thereof, for example selected from but not limited to, hepatic, thyroid, B-cell follicular lymphoma, lymph node, and bone metastases, and other solid tumors, preferably selected from breast cancer, renal/kidney cancer, multiple myeloma, brain tumor, lung cancer, ovarian cancer, colorectal cancer, bladder cancer and gastric cancer.

One embodiment is a method of diagnosing (including monitoring) a subject having PSMA related cancer, the method of diagnosis (monitoring) comprising administering to the subject the PSMA binding protein as described, optionally conjugated to radioactive molecules. In various embodiments, the PSMA binding protein as disclosed herein may be used for diagnosis of PSMA related cancer, optionally wherein the PSMA binding protein is conjugated to a radioactive molecule. In some embodiments, imaging methods using the PSMA binding protein with labels such as radioactive or fluorescent can be employed to visualize PSMA on specific tissues or cells, for example, to evaluate presence of PSMA related tumor cells, PSMA related tumor distribution, recurrence of PSMA related tumor, and/or to evaluate the response of a patient to a therapeutic treatment.

One embodiment is a method of treating a subject having PSMA related cancer, the method of treatment comprising administering to the subject the PSMA specific binding protein as described, optionally conjugated to a radioactive molecule and/or a cytotoxic agent. In various embodiments, the PSMA binding protein as disclosed herein may be used for treatment of PSMA related cancer, optionally wherein the PSMA binding protein is conjugated to a cytotoxic agent and/or to a radioactive molecule. Some embodiments relate to the use of the PSMA binding protein labelled with a suitable radioisotope or cytotoxic compound for treatment of PSMA related tumor cells, in particular to control or kill PSMA related tumor cells, for example malignant cells. In one embodiment, curative doses of radiation are selectively delivered to PSMA related tumor cells but not to normal cells.

Compositions.

Various embodiments relate to a composition comprising the PSMA binding protein as disclosed herein. A composition comprising the PSMA binding protein as defined above for use in medicine, preferably for use in the diagnosis or treatment of various PSMA related cancer tumors, such as in prostate cancer and metastases thereof, hepatic, thyroid, B-cell follicular lymphoma, lymph node, and bone metastases, renal/kidney cancer, multiple myeloma, brain tumor, lung cancer, ovarian cancer, colorectal cancer, bladder cancer, gastric cancer, and others. Compositions comprising the PSMA binding protein as described above may be used for clinical applications for both diagnostic and therapeutic purposes. In particular, compositions comprising the PSMA binding protein as described above may be used for clinical applications for imaging, monitoring, and eliminating or inactivating pathological cells that express PSMA.

Various embodiments relate to a diagnostic composition for the diagnosis of PSMA related cancer comprising the PSMA binding protein as defined herein and a diagnostically acceptable carrier and/or diluent. These include for example but are not limited to stabilizing agents, surface-active agents, salts, buffers, coloring agents etc. The compositions can be in the form of a liquid preparation, a lyophilisate, granules, in the form of an emulsion or a liposomal preparation.

The diagnostic composition comprising the PSMA binding protein as described herein can be used for diagnosis of PSMA related cancer, as described above.

Various embodiments relate to a pharmaceutical (e.g. therapeutical) composition for the treatment of diseases comprising the PSMA binding protein as disclosed herein, and a pharmaceutically (e.g. therapeutically) acceptable carrier and/or diluent. The pharmaceutical (e.g. therapeutical) composition optionally may contain further auxiliary agents and excipients known per se. These include for example but are not limited to stabilizing agents, surface-active agents, salts, buffers, coloring agents etc.

The pharmaceutical composition comprising the PSMA binding protein as defined herein can be used for treatment of diseases, as described above.

The compositions contain an effective dose of the PSMA binding protein as defined herein. The amount of protein to be administered depends on the organism, the type of disease, the age and weight of the patient and further factors known per se. Depending on the galenic preparation these compositions can be administered parentally by injection or infusion, systemically, intraperitoneally, intramuscularly, subcutaneously, transdermally, or by other conventionally employed methods of application.

The composition can be in the form of a liquid preparation, a lyophilisate, a cream, a lotion for topical application, an aerosol, in the form of powders, granules, in the form of an emulsion or a liposomal preparation. The type of preparation depends on the type of disease, the route of administration, the severity of the disease, the patient and other factors known to those skilled in the art of medicine.

The various components of the composition may be packaged as a kit with instructions for use.

Preparation of PSMA Binding Proteins.

PSMA binding proteins as described herein may be prepared by any of the many conventional and well known techniques such as plain organic synthetic strategies, solid phase-assisted synthesis techniques, fragment ligation techniques or by commercially available automated synthesizers. On the other hand, they may also be prepared by conventional recombinant techniques alone or in combination with conventional synthetic techniques. Furthermore, they may also be prepared by cell-free in vitro transcription/translation.

Various embodiments relate to a polynucleotide encoding a PSMA binding protein as disclosed herein. One embodiment further provides an expression vector comprising said polynucleotide, and a host cell comprising said isolated polynucleotide or the expression vector.

Various embodiments relate to a method for the production of a PSMA binding protein as disclosed herein comprising culturing of a host cell under suitable conditions which allow expression of said PSMA binding protein and optionally isolating said PSMA binding protein. For example, one or more polynucleotides which encode for the PSMA binding protein may be expressed in a suitable host and the produced PSMA binding protein can be isolated. A host cell comprises said nucleic acid molecule or vector.

Suitable host cells include prokaryotes or eukaryotes. A vector means any molecule or entity (e.g., nucleic acid, plasmid, bacteriophage or virus) that can be used to transfer protein coding information into a host cell. Various cell culture systems, for example but not limited to mammalian, yeast, plant, or insect, can also be employed to express recombinant proteins. Suitable conditions for culturing prokaryotic or eukaryotic host cells are well known to the person skilled in the art. Cultivation of cells and protein expression for the purpose of protein production can be performed at any scale, starting from small volume shaker flasks to large fermenters, applying technologies well-known to any skilled in the art. One embodiment is directed to a method for the preparation of a binding protein as detailed above, said method comprising the following steps: (a) preparing a nucleic acid encoding a PSMA binding protein as defined herein; (b) introducing said nucleic acid into an expression vector; (c) introducing said expression vector into a host cell; (d) cultivating the host cell; (e) subjecting the host cell to culturing conditions under which a PSMA binding protein is expressed, thereby producing a PSMA binding protein as defined herein; (f) optionally isolating the PSMA binding protein produced in step (e); and (g) optionally conjugating the PSMA binding protein with further functional moieties as defined herein.

In general, isolation of purified PSMA binding protein from the cultivation mixture can be performed applying conventional methods and technologies well known in the art, such as centrifugation, precipitation, flocculation, different embodiments of chromatography, filtration, dialysis, concentration and combinations thereof, and others. Chromatographic methods are well-known in the art and comprise without limitation ion exchange chromatography, gel filtration chromatography (size exclusion chromatography), or affinity chromatography.

For simplified purification, the PSMA binding protein can be fused to other peptide sequences having an increased affinity to separation materials. Preferably, such fusions are selected that do not have a detrimental effect on the functionality of the PSMA binding protein or can be separated after the purification due to the introduction of specific protease cleavage sites. Such methods are also known to those skilled in the art.

EXAMPLES

The following Examples are provided for further illustration of the invention. The invention is particularly exemplified by particular modifications of ubiquitin (SEQ ID NO: 1 or SEQ ID NO: 2) resulting in binding to PSMA. The invention, however, is not limited thereto, and the following Examples merely show the practicability of the invention on the basis of the above description.

Example 1. Identification of PSMA Binding Proteins

Library construction and cloning. Ubiquitin libraries comprising randomized amino acid positions were either synthesized by triplet technology (MorphoSys Slonomics, Germany) or in house by randomized oligonucleotides generated by synthetic trinucleotide phosphoramidites (ELLA Biotech) to achieve a well-balanced amino acid distribution with simultaneously exclusion of cysteine and other amino acid residues at randomized positions.

Several libraries were used to identify PSMA binding proteins library SPV2: Ubiquitin (SEQ ID NO: 1) randomized in amino acid positions 6, 8, 9, 10, 12, 42, 44, 46, 62, 63, 64, 65, 66, 68, 70, and 72.

library SPL27: Ubiquitin (SEQ ID NO: 1) randomized in amino acid corresponding to positions 62, 63, 64, 65, 66, 68, 70, and 72 and an insertion of six randomized amino acids introduced between T9 and G10 of ubiquitin. The occurrence of amino acid residues Cys, Ile, Leu, Val and Phe have been omitted in the insertion.

library SPVF19: Bis-ubiquitin (SEQ ID NO: 2) randomized in amino acid positions 6, 8, 62, 63, 64, 65, 66, 68, 70, 72, 82, 84, 138, 139, 140, 141, 142 (this corresponds to randomization of positions 6, 8, 62, 63, 64, 65, 66 in both ubiquitin moieties; in library SPVF19, two ubiquitin moieties are directly linked).

The corresponding cDNA library was amplified by PCR and ligated with a modified pCD87SA phagemid (herein referred to as pCD12) using standard methods known to a skilled person. The pCD12 phagemid comprises a modified torA leader sequence to achieve protein processing without additional amino acids at the N-terminus. Aliquots of the ligation mixture were used for electroporation of *Escherichia coli* ER2738 (Lucigen). Unless otherwise indicated, established recombinant genetic methods were used, for example as described in Sambrook, J & Russel, D. W. [2001] (Cold Spring Harbor Laboratory, NY.

Target Expression, Purification and Analysis.

A DNA sequence encoding the extracellular domain of human PSMA (uniprot Accession Number Q04609; residues 45-750) was genetically fused with the Fc region of human IgG$_1$ followed by a His-tag at the N-terminus. Full length cDNA with human codon usage was provided by GeneArt (Thermo Scientific), cloned into the mammalian expression vector pCEP4 and expressed in mammalian Expi293F cells at a scale of 250 ml in shaking flasks. Expression was analyzed by SDS-PAGE and by immunoblot analysis with antibodies directed against PSMA and the Fc-part of human IgG1. 130 ml cell culture supernatant of the large scale expression were centrifuged and filtrated for application to affinity chromatography on a Protein A HP 1 mL column (GE Healthcare). The target protein was eluted by a gentle pH shift (pH 4) and applied to a Superdex XK16/600 gel filtration column. 9 mg of His-Fc-PSMA could be recovered; SDS-PAGE analysis and SE-HPLC analysis confirmed the purity of the target protein. The enzymatic activity of the target protein towards the substrate N-acteyl-L-aspartyl-L-glutamate (NAAG) was confirmed.

Primary Selection by TAT Phage Display.

The naïve library was enriched against the target PSMA using TAT phage display as selection system. After transformation of competent bacterial ER2738 cells (Lucigene) with phagemid pCD12 carrying the library, phage amplification and purification was carried out using standard methods known to a skilled person. For selection the target protein was immobilized as Fc-fusion of the extracellular domain of human PSMA on Dynabeads® Protein A or Dynabeads® Protein G. The target concentration during phage incubation was lowered from 200 nM (first round) to 100 nM (second round) and 50 nM (third round) and 25 nM (fourth round). In some of the selection rounds mouse serum was added to select molecules with increased serum stability. Target phage complexes were magnetically separated from supernatant and washed several times. Target bound phages were eluted by trypsin. To deplete the phage library of Fc-binding variants a preselection of phages with immobilized Fc-fragment of IgG$_1$ (Athens Research & Technology) was performed prior to round two and three. To identify target specific phage pools, eluted and reamplified phages of each selection round were analysed by phage pool ELISA. Wells of a medium binding microtiter plate (Greiner Bio-One) were coated with PSMA-Fc (2.5 µg/ml) and Fc-fragment of IgG$_1$ (2.5 µg/ml), respectively. Bound phages were detected using α-M13 HRP-conjugated antibody (GE Healthcare).

Cloning of Target Binding Phage Pools into an Expression Vector.

Selection pools showing specific binding to the target in phage pool ELISA were amplified by PCR according to methods known in the art, cut with appropriate restriction nucleases and ligated into a derivative of the expression vector pET-28a (Merck, Germany) comprising a Strep-Tag II (IBA GmbH).

Single Colony Hit Analysis.

After transformation of BL21 (DE3) cells (Merck, Germany) kanamycin-resistant single colonies were grown. Expression of the target-binding modified ubiquitin variants was achieved by cultivation in 384 well plates (Greiner Bio-One) using auto induction medium. Cells were harvested and subsequently lysed chemically or enzymatically by BugBuster reagent (Novagen) and mechanically by freeze/thaw cycles, respectively. After centrifugation the resulting supernatants were screened by ELISA with immobilized target on High Bind 384 ELISA micrrotiter plates (Greiner Bio-One). Detection of bound protein was achieved by Strep-Tactin® HRP Conjugate (IBA GmbH) in combination with TMB-Plus Substrate (Biotrend, Germany). The reaction was stopped by addition of 0.2 M H$_2$SO$_4$ solution and measured in a plate reader at 450 nm versus 620 nm.

Construction of Maturation Library.

For maturation of each selected variant a module shuffling approach was used wherein the binding molecule is split into two modules. For ubiquitin muteins based on SEQ ID NO: 1, the first module comprises amino acids 1-40 and the second module amino acids 32-76. For bis-ubiquitin muteins based on SEQ ID NO: 2, the first module comprises amino acids 1-77 and the second module amino acids 71-152. For cloning of the module shuffling maturation libraries either module one of the variants was kept constant and fused with a native second module of the original library or vice versa. The fusion of the two modules was achieved by overlap extension PCR. The obtained cDNA of maturation libraries was ligated with pCD12 as described above. Alternatively, an error prone PCR approach was used where additional mutations in predefinded molecules or pools were induced.

Maturation Selection and Analysis.

For affinity maturation two rounds of panning were performed. For both rounds a preselection with Fc-fragment of IgG$_1$ was performed. In some of the selection rounds mouse serum was added to select molecules with increased serum stability. To analyse the matured and selected pools for specific target binding a phage pool ELISA was performed followed by cloning of positive pools into expression vector pET-28a and hit ELISA as described above.

Example 2. Expression and Purification of PSMA-Binding Proteins

PSMA binding molecules were cloned into an expression vector using standard methods known to a skilled person, purified and analyzed as described below.

All constructs were expressed in *Escherichia coli* BL21 (DE3) using a low copy plasmid system under regulation of a T7 promoter. Proteins were produced cytoplasmatically in mostly soluble form after induction by lactose included in the medium (autoinduction medium). All overnight cultures were inoculated from a single colony after a fresh transformation with a defined plasmid. PSMA binding proteins were produced in ZYM5052 autoinduction medium according to Studier et al. (2005). Overnight cultures were grown up to saturation in shake flasks in a volume of 20-100 mL in 2×YT medium. Main cultures were inoculated to an OD600 of 0.05 to 0.1 and incubated in ZYM5052 with 50 µg/mL kanamycin for up to 24 h at 30° C. on a rotary shaker at 200 rpm in shake flasks with or without baffles. Depending on the expression levels either in 1 L shake flasks with 350 mL medium each or 5 L flasks with 1 L medium each.

Affilin proteins with affinity tag were purified by affinity chromatography and gel filtration. After affinity chromatography purification a size exclusion chromatography (SE HPLC or SEC) has been performed using an Äkta system and a Superdex™ 200 HiLoad 16/600 column (GE Healthcare). The column has a volume of 120 ml and was equilibrated with 2 CV. The samples were applied with a flow rate of 1 ml/min. Fraction collection starts as the signal intensity reaches 10 mAU. Following SDS-PAGE analysis positive fractions were pooled and their protein concentrations were measured.

Dimeric PSMA binding proteins without affinity tag were purified using cation exchange chromatography (SP Sepharose HP, GE Healthcare) followed by anion exchange chromatography (Q Sepharose HP, GE Healthcare) to reduce the amount of endotoxin.

Finally, a size exclusion chromatography (Sephacryl S200HR, GE Healthcare) was performed. Further analysis included SDS-PAGE, SE-HPLC and RP-HPLC. Protein concentrations were determined by absorbance measurement at 280 nm using the molar absorbent coefficient. For example, the purity of SEQ ID NO: 5 is 98% according to SE-HPLC. RP chromatography (RP-HPLC) has been performed using a Dionex HPLC system and a PLRP-S (5 µm, 300 Å) column (Agilents).

Example 3. PSMA Binding Proteins are Stable at High Temperatures

Thermal stability of the binding proteins of the invention was determined by Differential Scanning Fluorimetry (DSF). Each sample was transferred at concentrations of 0.1 µg/µL to a LightCycler® 480 Multiwell Plate 96 (Roche), and SYPRO Orange dye was added at suitable dilution. A temperature ramp from 20 to 90° C. was programmed with a heating rate of 1° C. per minute (LightCycler® 480, Roche). Fluorescence was constantly measured at an excitation wavelength of 465 nm and the emission wavelength at 580 nm (LightCycler® 480, Roche). The midpoints of transition for the thermal unfolding (Tm, melting points) are shown for selected muteins in FIG. 1, FIG. 2, and FIG. 3. PSMA binding proteins of the invention have melting temperatures up to 85° C. The $T_m$ of SEQ ID NO: 5 is 69.3° C. and the $T_m$ of SEQ ID NO: 6 is 84.2° C. See Table 2 for temperature stability of selected dimeric PSMA binding proteins.

Example 4. Analysis of PSMA Binding Proteins (Surface Plasmon Resonance, SPR)

A CM5 sensor chip (GE Healthcare) was equilibrated with SPR running buffer. Surface-exposed carboxylic groups were activated by passing a mixture of EDC and NHS to yield reactive ester groups. 700-1500 RU PSMA-Fc (on-ligand) were immobilized on a flow cell, IgG-Fc (offligand) was immobilized on another flow cell at a ratio of 1:3 (hIgG-Fc:Target) to the target. Injection of ethanolamine after ligand immobilization was used to block unreacted NHS groups. Upon ligand binding, protein analyte was accumulated on the surface increasing the refractive index. This change in the refractive index was measured in real time and plotted as response or resonance units (RU) versus time. The analytes were applied to the chip in serial dilutions with a flow rate of 30 µl/min. The association was performed for 120 seconds and the dissociation for 360 seconds. After each run, the chip surface was regenerated with 30 µl regeneration buffer and equilibrated with running buffer. A dilution series served as positive control, whereas a dilution series of unmodified ubiquitin represents the negative control. The control samples were applied to the matrix with a flow rate of 30 µl/min, while they associate for 60 seconds and dissociate for 120 seconds. Regeneration and re-equilibration were performed as previously mentioned. Binding studies were carried out by the use of the Biacore 3000 (GE Healthcare); data evaluation was operated via the BIAevaluation 3.0 software, provided by the manufacturer, by the use of the Langmuir 1:1 model (RI=0). After fitting the data with a 1:1 langmuir model, for example, $K_D$ values were calculated and shown in FIG. 1, FIG. 2, FIG. 3, and Table 2. Evaluated dissociation constants ($K_D$) were standardized against off-target and indicated. For example, the $K_D$ of SEQ ID NO: 5 is 1.8 nM vs. hPSMA-Fc (1100 RU immobilized via Protein A), the $K_D$ of SEQ ID NO: 6 is 113 nM, the $K_D$ of SEQ ID NO: 22 is 484 nM, the $K_D$ of SEQ ID NO: 45 is 33 nM, and $K_D$ of SEQ ID NO: 26 is 9.3 nM. Table 2 shows binding affinity as determined by SPR and temperature stability (see Example 3) of dimeric PSMA binding proteins.

TABLE 2

| | Binding affinity and temperature stability of dimeric PSMA binding proteins | | |
|---|---|---|---|
| SEQ ID NO: | Dimer of | Affinity to PSMA (M) | DSF (° C.) |
| 52 | SEQ ID NO: 3 | 2.94 e-13 | 68.04 |
| 53 | SEQ ID NO: 25 | 5.17 e-13 | 64.02 |
| 54 | SEQ ID NO: 25 and SEQ ID NO: 3 | 6.32 e-12 | 77.60 |
| 55 | SEQ ID NO: 3 and SEQ ID NO: 25 | 8.27 e-14 | 76.93 |

Example 5. Functional Characterization: Binding to Cell Surface Expressed PSMA (Flow Cytometry)

Flow cytometry was used to analyze the binding of PSMA binding proteins to cell surface-exposed PSMA. PSMA overexpressing human prostate carcinoma cell line LNCaP, PSMA overexpressing transfected HEK293-PSMA-cells, PSMA non-expressing PC3-cells and empty vector control HEK293-pEntry-cells were used. Cells were trypsinized and resuspended in medium containing FCS, washed and stained in pre-cooled FACS blocking buffer. A cell concentration of 1×10⁶ cells/ml was prepared for cell staining and 100 µl were respectively filled into the wells of a 96 well plate (Greiner) in triplicate for each cell line. Different concentrations, for example 50 nM of PSMA binding proteins or 0.5 µg/ml monoclonal anti-human-PSMA antibody (clone LNI-17; Biolegend; 342502) as positive control were added to PSMA overexpressing and control cells in several experiments. PSMA-binding proteins included C-terminal Strep-tags (see e.g. SEQ ID NO: 71) for purification and detection purposes. After 45 min the supernatants were removed and 100 μl/well rabbit anti-Strep-Tag antibody (obtained from GenScript; A00626), 1:300 diluted in FACS blocking buffer were added. Anti-PSMA antibody was detected with anti-mouse-IgG-Alexa 488 (Invitrogen; A-10680) with a dilution of 1:1000 in the positive control wells. After removal of the anti-Strep-Tag antibody from the other wells goat anti-rabbit IgG Alexa Fluor 488 antibody (obtained from Invitrogen; A11008) was applied in a 1:1000 dilution. Flow cytometry measurement was conducted on the Guava easyCyte 5HT device from Merck-Millipore at excitation wavelength 488 nm and emission wavelength 525/30 nm. All PSMA binding proteins of the invention (including dimers) showed binding to surface expressed PSMA on LNCaP-cells and HEK293-PSMA-cells (see FIG. 1, FIG. 2, FIG. 3; binding is indicated in the Figures by "yes") and no binding on PSMA-negative cell lines HEK293-pEntry or PC3 cells. Ubiquitin showed no binding on LNCaP-cells and HEK293-PSMA-cells. Positive binding on PSMA-expressing cells was also observed for anti-PSMA-antibody. For example, SEQ ID NO: 4 showed strong cell binding to HEK-PSMA and LNCaP cells.

Example 6. Binding to Cell Surface Expressed PSMA (Immunocytochemistry and Fluorescence Microscopy)

A concentration of 50 nM was tested on PSMA-expressing LNCaP-cells and control cell line PC3 (no PSMA expression). Bis-Ubiquitin was used as control for a non-PSMA-binding protein and 1 μg/ml anti-PSMA-ab served as positive control for PSMA binding. Cells were seeded with a concentration of $1\times10^5$ cells/ml in Poly-D-Lysin coated Lab-Tek® Chamber-Slides (Sigma-Aldrich). After cultivation over 72 h the cells were fixed with methanol (5 min, −20° C.), followed by blocking (5% Fetal Horse Serum in PBS, 1 h) and incubation with 50 nM PSMA binding protein for 45 min at rt. PSMA binding was detected by incubation with rabbit-anti-Strep-Tag-antibody (1:500) for 1 h and subsequently with anti-rabbit-IgG-Alexa488-antibody (1:1000) for 1 h. The nuclei were stained with 4 μg/ml DAPI. All incubation steps were done at room temperature. PSMA binding of dimer SEQ ID NO: 54, dimer SEQ ID NO: 55 and monomer SEQ ID NO: 25 on LNCaP-cells was confirmed, whereas no binding to PC3-cells could be observed.

Example 7. Functional Characterization: PSMA Binding Proteins Bind to PSMA that is Expressed on Tumor Tissue (Immunohistochemistry)

Tissue sections of frozen LNCaP-xenograft-tumor and F9-syngraft-tumor slices were used to analyze binding proteins of the invention. Tissue slices were fixed with ice-cold acetone for 10 min. Dimers of PSMA-binding proteins included C-terminal Strep-tags (see e.g. SEQ ID NO: 71) for purification and detection purposes. After blocking and incubation with 50 nM and 10 nM of dimer of SEQ ID NO: 54, 100 nM and 10 nM of dimers of SEQ ID NOs: 52 and SEQ ID NO: 53 and 100 nM of control protein unmodified bis-ubiquitin, slices were incubated with rabbit anti-StrepTag-antibody (1:500) for 1 h. Sections were then processed with Novolink™ Polymer (Leica, RE7290-CE). The slices were incubated with AEC-solution (DAKO) for 1 min to visualize binding of proteins. Nuclei were stained with Mayer's hemalum solution (Merck Millipore, cat-no. 109249). All incubation steps were done at room temperature. 2 μg/ml of anti-PSMA-ab GCP-04 (Novus Biologicals) and 14 μg/ml GCP-05 (Thermo Scientific) served as positive control. Strong PSMA binding of 50 nM heterodimer (SEQ ID NO: 54) and 100 nM homodimers (SEQ ID NO: 52 and SEQ ID NO: 53) on LNCaP-tumor tissue was confirmed. The anti-PSMA-antibodies GCP-04 and GCP-05 showed the same staining pattern whereas unmodified ubiquitin showed no staining. No unspecific staining on F9-tumor tissue was observed.

Example 8. Competition Analysis of PSMA Binding Proteins

To investigate whether the isolated PSMA-Affilin-proteins bind to identical or different PSMA epitopes, the following assay was performed: PSMA-Fc fusion protein (60 nM) was immobilized on a CM5 Biacore chip that was coupled with recombinant Protein A using NHS/EDC chemistry resulting in 1000 response units (RU). In a first experiment, SEQ ID NO: 25 (motif KHNTW) and SEQ ID NO: 15 (motif GFAHR and WTTTF) were injected at one defined concentration (0.5 μM) at a flow of 30 μl/min PBST 0.005% Tween 20. In the second experiment, the same flow channel was first pre-loaded with 500 nM SEQ ID NO: 25 until the chip surface was saturated. In the next step, 500 nM SEQ ID NO: 15 was identically applied as in the first experiment. Alternatively, in the second experiment, the same flow channel was first pre-loaded with 500 nM SEQ ID NO: 15 until the chip surface was saturated, followed by loading of 500 nM SEQ ID NO: 25.

The experiment showed that the binding of a PSMA binding protein with motif KHNTW was not influenced by the presence of a PSMA binding protein with motif GFAHR and WTTTF, and vice versa. Thus, no competition was observed that leads to the conclusion that these PSMA binding proteins bind to different or non-overlapping PSMA-epitopes, i.e. to different surface exposed amino acids.

Example 9: Labeling of Fusion Protein with DOTA

Dimeric proteins were incubated with 20-fold excess of Maleimide-DOTA (2,2',2''-(10-(2-((2-(2,5-dioxo-2,5-di-hydro-1H-pyrrol-1-yl)ethyl)amino)-2-oxoethyl)-1,4,7,10-tetraazacyclododecane-1,4,7-triyl)triacetic acid, CheMatech) in 50 mM HEPES, 150 mM sodium chloride, 5 mM EDTA pH 7.0 for 3 h at room temperature. In order to reduce metal ions that might interact with DOTA-molecules all columns and AKTA devices (GE Healthcare) were incubated with 0.1 M EDTA solution for 30 minutes. For preparing solutions only metal-free or metal-reduced components were used. After incubation the samples were separated from unbound DOTA molecules via gelfiltration (Superdex S200, GE Healthcare) in 100 mM sodium acetate pH 5.0-5.8. Samples of labeled proteins were also incubated with 5 mM iron(II)chloride for 1 h at room temperature to prove that DOTA-molecules are available for coupling with radio isotopes. After the incubation unbound iron was removed using a HiTrap Desalting column (GE Healthcare). MALDI-TOF analysis was used to determine the degree of labeling.

Example 10: Matrix-Assisted Laser Desorption/Ionization Mass Spectrometry (MALDI-TOF) Mass Spectrometry Matrix-assisted laser desorption/ionization mass spectrometry (MALDI-TOF MS) was carried out as followed: Fusion proteins were purified and concentrated using C18-P10-ZipTips (Millipore; catalog number ZTC18S096). The tips were washed with 0.1% (v/v) trifluoroacidic acid (TFA) in water and eluted with 50% (v/v) acetonitrile/0,1% TFA. Samples were treated with 2% (v/v) TFA in water and embedded in 2,5-dihydroxyacetophenone (DHAP) matrix (Bruker, catalog number 8231829). The mass of fusion proteins was measured on an Autoflex™ speed mass spectrometer (Bruker). Protein calibration standards (Bruker, part no. 8206355 and part no. 8207234) were used for tuning of the autoflex speed mass spectrometer.

Fusion proteins with and without DOTA label were analyzed by MALDI-TOF mass spectra and peaks were compared. MALDI-TOF analysis shows that the DOTA molecules labeled to the dimeric PSMA-binding proteins are available for coupling with iron(II)chloride molecules.

Although the $K_D$ is slightly altered after labeling of the fusion proteins, labeling does not significantly affect the affinity of the fusion proteins to the target. Results are summarized in Table 3.

TABLE 3

Affinity analysis of labelled PSMA binding proteins using SPR

| SEQ ID NO: | label | $Mr_{calc}$ | $Mr_{exp}$ | target affinity $K_D$ |
|---|---|---|---|---|
| 5 | none | | | 1.8 nM |
| 5 | DOTA | | | 4.2 nM |
| 52 | none | 43027 Da | 43019 Da | 2.94 e−13M |
| 52 | DOTA | 44080 Da | 44072 Da | 2.99 e−14M |
| 52 | DOTA + iron | 44192 Da | 44178 Da | n.d. |
| 54 | none | 35209 Da | 35216 Da | 6.32 e−12M |
| 54 | DOTA | 36263 Da | 36266 Da | 6.39 e−10M |
| 54 | DOTA + iron | 36374 Da | 36363 Da | n.d. |
| 55 | none | 27391 Da | 27384 Da | 8.27 e−14M |
| 55 | DOTA | 28444 Da | 28433 Da | 2.04 e−13M |
| 55 | DOTA + iron | 28556 Da | 28535 Da | n.d. |

Example 11. Serum Stability of PSMA Binding Proteins (Flow Cytometry)

The stability of PSMA binding proteins even in the presence of serum was analyzed. PSMA-binding proteins included C-terminal FLAG-tags (DYKDDDDK; see e.g. SEQ ID NO: 78) for purification and detection purposes. PSMA binding proteins based on ubiquitin muteins with GFAHR, or a motif with 80% identity thereto, e.g. SEQ ID NO: 4 or SEQ ID NO: 11, were incubated with a dilution series from 1 μM to 5.6 μM in 100% mouse serum for 0 h or for 24 h at 37° C. 100 μl Affilin-serum solution was used to analyze the serum stability on HEK293-PSMA-cells. After supernatants were removed, binding was proven with 1 μg/ml anti-FlagTag-ab (Sigma-Aldrich; F1804) and anti-mouse-IgG-Alexa488 (Invitrogen; A10680). FACS analysis confirmed PSMA binding even after 24 h incubation in mouse serum (see Table 4). Further PSMA binding proteins were tested and binding to PSMA was confirmed also in the presence of serum.

TABLE 4

Binding of PSMA binding proteins in the presence of serum (Flow cytometry)

| SEQ ID NO: | EC50 (0 h) nM | EC50 (24 h) nM | Decrease (fold) | Serum stability |
|---|---|---|---|---|
| 4 | 1.6 | 4.5 | 2.8 | yes |
| 11 | 2.6 | 6.6 | 2.5 | yes |

Example 12. Serum Stability of PSMA Binding Proteins (ELISA)

High binding 96 well plates (Greiner, 781061) were immobilized with 2.5 μg/ml PSMA-Fc over night at 4° C. Dilution series of Affilin-191871 (with c-terminal SAC; SEQ ID NO: 5) and SEQ ID NO: 5 Dota labeled with Lutetium Lu3+ were incubated in 100% mouse serum overnight at 37° C. ELISA-plates were washed with 1×PBS and blocked with 3% BSA/0.5% Tween/PBS 2 h at RT. Dilution series after 0 h or 24 h incubation in the presence of serum were incubated on ELISA-plates 1 h at rt. After washing with PBST, wells were incubated with biotinylated anti-ubiquitin-antibody (1:1000) 1 h at rt. The binding was visualized with Streptavidin-HRP (1:10.000). The PSMA binding proteins show no significant shift of $K_D$ after 24 h serum incubation. For example, ELISA analysis confirmed the binding of SEQ ID NO: 5 and SEQ ID NO: 5 Dota labeled with Lutetium Lu3+ to PSMA even after 24 h incubation in mouse serum with $K_D$ of 0.75+/−0.02 (compared to a $K_D$ of 0.53+/−0.02 at 0 h incubation in mouse serum).

The invention claimed is:

1. A prostate specific membrane antigen (PSMA) binding protein, comprising an amino acid sequence that is identical to any one of SEQ ID NOs: 3-7, 9-15, 19-22, 52, and 55, provided that the amino acid sequence that is identical to any one of SEQ ID NOs: 3-7, 9-15, 19-22, 52, and 55 comprises an amino acid binding motif selected from the group consisting of GFAHR (SEQ ID NO: 56), GWAHR (SEQ ID NO: 57), or SYAHR (SEQ ID NO: 73) at amino acid residues that correspond to amino acid positions 62, 63, 64, 65, 66 of any one of SEQ ID NOs: 3-7, 9-15, 19-22, 52, and 55, and wherein the PSMA binding protein has a specific binding affinity to the extracellular domain of PSMA of 1 nM to 500 nM.

2. The PSMA binding protein according to claim 1, wherein the PSMA binding protein is a multimer comprising of a plurality of the PSMA binding protein according to claim 1.

3. The PSMA binding protein according to claim 1, wherein the PSMA binding protein is a dimer of the PSMA binding protein according to claim 1.

4. The PSMA binding protein according to claim 1, further comprising one or more coupling sites for the coupling of chemical moieties.

5. The PSMA binding protein according to claim 1, further comprising at least one diagnostically active moiety or at least one therapeutically active moiety.

6. The PSMA binding protein according to claim 1, further comprising at least one moiety modulating pharmacokinetics.

7. The PSMA binding protein according to claim 1, for use in diagnosis or treatment of PSMA related tumors.

8. The PSMA binding protein according to claim 4, wherein the chemical moieties are selected from the group consisting of chelators, drugs, toxins, dyes, and small molecules.

9. The PSMA binding protein according to claim 5, wherein the at least one diagnostically active moiety is selected from the group consisting of a radionuclide, a fluorescent protein, a photosensitizer, a dye, and an enzyme, or any combination thereof.

10. The PSMA binding protein according to claim 5, wherein the at least one therapeutically active moiety is selected from the group consisting of a monoclonal antibody or fragment thereof, a binding protein, a radionuclide, a cytotoxic compound, a cytokine, a chemokine, an enzyme, and derivatives thereof, or any combination thereof.

11. The PSMA binding protein according to claim 6, wherein the at least one moiety modulating pharmacokinetics is selected from the group consisting of a polyethylene glycol, a human serum albumin, an albumin-binding protein, an immunoglobulin binding protein, an immunoglobulin or fragment thereof, a polysaccharide, and an amino acid sequence comprising amino acids selected only from the group consisting of alanine, serine, proline, and glycine.

12. A composition comprising the PSMA binding protein according to claim 1 for use in medicine.

13. A method for producing the PSMA binding protein according to claim 1, the method comprising (a) culturing a host cell under conditions suitable to obtain said PSMA binding protein; and (b) isolating said PSMA binding protein produced.

14. A method for imaging a tumor that expresses PSMA, the method comprising contacting the tumor with a composition comprising the PSMA binding protein according to claim 1 conjugated to a detectable moiety.

15. A method for radiotherapy of a PSMA related tumor, the method comprising contacting the PSMA related tumor with a composition comprising the PSMA binding protein according to claim 1 conjugated to a radionuclide, optionally via a chelator.

* * * * *